US011752004B2

(12) United States Patent
Oglaza et al.

(10) Patent No.: US 11,752,004 B2
(45) Date of Patent: Sep. 12, 2023

(54) SYSTEMS AND IMPLANTS FOR BONE RESTORATION

(71) Applicant: Stryker European Operations Limited, Carrigtwohill (IE)

(72) Inventors: Jean-François Oglaza, Portage, MI (US); Christian Renaud, Arthes (FR); Alain Leonard, Caixon (FR); Gildas Huet, Chantilly (FR)

(73) Assignee: Stryker European Operations Limited, Carrigtwohill (IE)

( * ) Notice: Subject to any disclaimer, the term of this patent is extended or adjusted under 35 U.S.C. 154(b) by 372 days.

(21) Appl. No.: 17/071,352

(22) Filed: Oct. 15, 2020

(65) Prior Publication Data

US 2021/0022884 A1 Jan. 28, 2021

Related U.S. Application Data

(63) Continuation of application No. 16/126,371, filed on Sep. 10, 2018, now Pat. No. 10,813,771, which is a (Continued)

(30) Foreign Application Priority Data

Jun. 9, 2004 (FR) ..................... 0406211

(51) Int. Cl.
*A61F 2/44* (2006.01)
*A61B 17/88* (2006.01)
(Continued)

(52) U.S. Cl.
CPC ........ *A61F 2/4425* (2013.01); *A61B 17/8858* (2013.01); *A61F 2/44* (2013.01);
(Continued)

(58) Field of Classification Search
CPC ........ A61F 2/4425; A61F 2/44; A61F 2/4611; A61F 2002/30556; A61F 2002/30593
(Continued)

(56) References Cited

U.S. PATENT DOCUMENTS 4,796,612 A 1/1989 Reese
4,932,975 A 6/1990 Main et al.
(Continued)

FOREIGN PATENT DOCUMENTS

AU 705930 B2 6/1999
CN 1162349 A 10/1997
(Continued)

OTHER PUBLICATIONS

Chinese Search Report for Application 201480070702.5 dated Feb. 2, 2018.
(Continued)

*Primary Examiner* — Eduardo C Robert
*Assistant Examiner* — Tara Rose E Carter
(74) *Attorney, Agent, or Firm* — Howard & Howard Attorneys PLLC

(57) ABSTRACT

A system configured to increase height of a vertebral body. An implant includes plates each defining a bearing surface configured to be moved away from one another to expand the implant within the vertebral body. Supports are each coupled to one of the plates and include a reduced thickness portion defining a material web configured to plastically deform during expansion of the implant. The system includes an implant carrier with which an end element of the implant is removably coupled, and a rod configured to be translated relative to the implant carrier to cause expansion of the implant. An opposed portion may be coupled to the supports and configured to receive a longitudinal force to be moved relative to the end element. Second supports may be
(Continued)

each coupled to the end element and one of the plates. Each of the second supports may plastically deform during expansion of the implant.

23 Claims, 14 Drawing Sheets

Related U.S. Application Data continuation of application No. 15/194,440, filed on Jun. 27, 2016, now Pat. No. 10,098,751, which is a continuation of application No. 12/938,993, filed on Nov. 3, 2010, now Pat. No. 9,408,707, which is a continuation of application No. 11/150,676, filed on Jun. 9, 2005, now Pat. No. 7,846,206, which is a continuation-in-part of application No. 10/951,766, filed on Sep. 29, 2004, now abandoned.

(51) Int. Cl.
  A61F 2/46       (2006.01)
  A61B 17/70      (2006.01)
  A61F 2/30       (2006.01)

(52) U.S. Cl.
  CPC ............ A61F 2/442 (2013.01); A61F 2/4601 (2013.01); A61F 2/4611 (2013.01); A61B 17/70 (2013.01); A61F 2002/30224 (2013.01); A61F 2002/30471 (2013.01); A61F 2002/30556 (2013.01); A61F 2002/30579 (2013.01); A61F 2002/30593 (2013.01); A61F 2002/30601 (2013.01); A61F 2002/30617 (2013.01); A61F 2002/30772 (2013.01); A61F 2002/30774 (2013.01); A61F 2002/4627 (2013.01); A61F 2002/4629 (2013.01); A61F 2002/4635 (2013.01); A61F 2220/0091 (2013.01); A61F 2230/0069 (2013.01); A61F 2250/0009 (2013.01); A61F 2310/00023 (2013.01)

(58) Field of Classification Search
  USPC .................. 606/246–249; 623/17.11–17.16
  See application file for complete search history.

(56) References Cited

U.S. PATENT DOCUMENTS

| | | | |
|---|---|---|---|
| 4,961,740 A | 10/1990 | Ray et al. | |
| 4,969,888 A | 11/1990 | Scholten et al. | |
| 5,059,193 A | 10/1991 | Kuslich | |
| 5,108,395 A | 4/1992 | Laurain | |
| 5,108,404 A | 4/1992 | Scholten et al. | |
| 5,209,753 A | 5/1993 | Biedermann et al. | |
| 5,649,902 A | 7/1997 | Yoon | |
| 5,665,122 A | 9/1997 | Kambin | |
| 5,693,100 A | 12/1997 | Pisharodi | |
| 5,695,515 A | 12/1997 | Orejola | |
| 5,704,860 A | 1/1998 | Stief | |
| 5,713,907 A | 2/1998 | Hogendijk et al. | |
| 5,720,746 A | 2/1998 | Soubeiran | |
| 5,749,916 A | 5/1998 | Richelsoph | |
| 5,800,500 A | 9/1998 | Spelman et al. | |
| 5,800,550 A | 9/1998 | Sertich | |
| 5,908,448 A | 6/1999 | Roberts et al. | |
| 5,972,015 A | 10/1999 | Scribner et al. | |
| 5,980,522 A | 11/1999 | Koros et al. | |
| 6,039,761 A | 3/2000 | Li et al. | |
| 6,066,154 A | 5/2000 | Reiley et al. | |
| 6,102,950 A | 8/2000 | Vaccaro | |
| 6,126,689 A | 10/2000 | Brett | |
| 6,127,597 A | 10/2000 | Beyar et al. | |
| 6,176,882 B1 | 1/2001 | Biedermann et al. | |
| 6,183,517 B1 | 2/2001 | Suddaby | |
| 6,190,414 B1 | 2/2001 | Young et al. | |
| 6,193,757 B1 | 2/2001 | Foley et al. | |
| 6,197,033 B1 | 3/2001 | Haid, Jr. et al. | |
| 6,214,050 B1 | 4/2001 | Huene | |
| 6,235,043 B1 | 5/2001 | Reiley et al. | |
| 6,248,110 B1 | 6/2001 | Reiley et al. | |
| 6,261,289 B1 | 7/2001 | Levy | |
| 6,280,456 B1 | 8/2001 | Scribner et al. | |
| 6,332,895 B1 | 12/2001 | Suddaby | |
| 6,346,109 B1 | 2/2002 | Fucci et al. | |
| 6,395,031 B1 | 5/2002 | Foley et al. | |
| 6,423,083 B2 | 7/2002 | Reiley et al. | |
| 6,454,807 B1 | 9/2002 | Jackson | |
| 6,488,710 B2 | 12/2002 | Besselink | |
| 6,554,833 B2 | 4/2003 | Levy et al. | |
| 6,582,431 B1 | 6/2003 | Ray | |
| 6,595,998 B2 | 7/2003 | Johnson et al. | |
| 6,599,294 B2 | 7/2003 | Fuss et al. | |
| 6,607,544 B1 | 8/2003 | Boucher et al. | |
| 6,623,505 B2 | 9/2003 | Scribner et al. | |
| 6,632,235 B2 | 10/2003 | Weikel et al. | |
| 6,663,647 B2 | 12/2003 | Reiley et al. | |
| 6,664,897 B2 | 12/2003 | Pape et al. | |
| 6,676,665 B2 | 1/2004 | Foley et al. | |
| 6,716,216 B1 | 4/2004 | Boucher et al. | |
| 6,719,773 B1 | 4/2004 | Boucher et al. | |
| 6,726,691 B2 | 4/2004 | Osorio et al. | |
| 6,730,126 B2 | 5/2004 | Boehm, Jr. et al. | |
| 6,740,093 B2 | 5/2004 | Hochschuler et al. | |
| 6,749,595 B1 | 6/2004 | Murphy | |
| 6,783,530 B1 | 8/2004 | Levy | |
| 6,929,647 B2 | 8/2005 | Cohen | |
| 6,953,477 B2 | 10/2005 | Berry | |
| 6,979,341 B2 | 12/2005 | Scribner et al. | |
| 6,981,981 B2 | 1/2006 | Reiley et al. | |
| 7,044,954 B2 | 5/2006 | Reiley et al. | |
| 7,070,598 B2 | 7/2006 | Lim et al. | |
| 7,083,650 B2 | 8/2006 | Moskowitz et al. | |
| 7,087,055 B2 | 8/2006 | Lim et al. | |
| 7,153,306 B2 | 12/2006 | Ralph et al. | |
| 7,217,293 B2 | 5/2007 | Branch, Jr. | |
| 7,226,481 B2 | 6/2007 | Kuslich | |
| 7,234,468 B2 | 6/2007 | Johnson et al. | |
| 7,241,303 B2 | 7/2007 | Reiss et al. | |
| 7,261,720 B2 | 8/2007 | Stevens et al. | |
| 7,264,622 B2 | 9/2007 | Michelson | |
| 7,318,839 B2 | 1/2008 | Malberg et al. | |
| 7,507,241 B2 | 3/2009 | Levy et al. | |
| 7,513,900 B2 | 4/2009 | Carrison et al. | |
| 7,591,822 B2 | 9/2009 | Olson, Jr. et al. | |
| 7,621,950 B1 | 11/2009 | Globerman et al. | |
| 7,625,377 B2 | 12/2009 | Veldhuizen et al. | |
| 7,727,279 B2 | 6/2010 | Zipnick et al. | |
| 7,744,637 B2 | 6/2010 | Johnson et al. | |
| 7,749,255 B2 | 7/2010 | Johnson et al. | |
| 7,758,644 B2 | 7/2010 | Trieu | |
| 7,763,028 B2 | 7/2010 | Lim et al. | |
| 7,763,074 B2 | 7/2010 | Altarac et al. | |
| 7,799,080 B2 | 9/2010 | Doty | |
| 7,846,206 B2 * | 12/2010 | Oglaza .................... A61F 2/44 623/17.11 |
| 7,879,104 B2 | 2/2011 | Dewey et al. | |
| 7,901,409 B2 | 3/2011 | Canaveral et al. | |
| 7,905,885 B2 | 3/2011 | Johnson et al. | |
| 8,133,232 B2 | 3/2012 | Levy et al. | |
| 8,152,813 B2 | 4/2012 | Osorio et al. | |
| 8,236,058 B2 | 8/2012 | Fabian et al. | |
| 8,282,520 B2 | 10/2012 | Kurematsu et al. | |
| 8,292,890 B2 | 10/2012 | Wu | |
| 8,317,802 B1 | 11/2012 | Manzi et al. | |
| 8,323,309 B2 | 12/2012 | Khairkhahan et al. | |
| 8,328,818 B1 | 12/2012 | Seifert et al. | |
| 8,372,115 B2 | 2/2013 | Kohm et al. | |
| 8,409,282 B2 | 4/2013 | Kim | |
| 8,425,559 B2 | 4/2013 | Tebbe et al. | |
| 8,491,591 B2 | 7/2013 | Furderer | |
| 8,628,577 B1 | 1/2014 | Jimenez | |
| 8,636,746 B2 | 1/2014 | Jimenez et al. | |

(56) References Cited

U.S. PATENT DOCUMENTS

| | | |
|---|---|---|
| 8,709,086 B2 | 4/2014 | Glerum |
| 8,784,491 B2 | 7/2014 | Biedermann et al. |
| 8,864,833 B2 | 10/2014 | Glerum et al. |
| 8,888,853 B2 | 11/2014 | Glerum et al. |
| 8,932,302 B2 | 1/2015 | Jimenez et al. |
| 8,940,048 B2 | 1/2015 | Butler et al. |
| 8,945,190 B2 | 2/2015 | Culbert et al. |
| 8,961,609 B2 | 2/2015 | Schaller |
| 8,986,386 B2 | 3/2015 | Oglaza et al. |
| 8,998,923 B2 | 4/2015 | Chirico et al. |
| 9,034,041 B2 | 5/2015 | Wolters et al. |
| 9,173,747 B2 | 11/2015 | Hansell et al. |
| 9,295,502 B2 | 3/2016 | Fuerderer |
| 9,326,806 B2 | 5/2016 | Lin et al. |
| 9,408,707 B2 * | 8/2016 | Oglaza ................. A61F 2/4611 |
| 9,439,770 B2 | 9/2016 | Biedermann et al. |
| 9,445,856 B2 | 9/2016 | Seifert et al. |
| 9,526,621 B2 | 12/2016 | Kuslich |
| 10,098,751 B2 * | 10/2018 | Oglaza .................... A61F 2/442 |
| 10,813,771 B2 * | 10/2020 | Oglaza ................. A61F 2/4425 |
| 2001/0020186 A1 | 9/2001 | Boyce et al. |
| 2001/0032020 A1 * | 10/2001 | Besselink ............. A61F 2/4455 |
| | | 623/17.15 |
| 2002/0058947 A1 | 5/2002 | Hochschuler et al. |
| 2002/0065548 A1 | 5/2002 | Birdsall et al. |
| 2002/0068974 A1 | 6/2002 | Kuslich et al. |
| 2002/0120327 A1 | 8/2002 | Cox et al. |
| 2002/0143401 A1 | 10/2002 | Michelson |
| 2002/0151976 A1 | 10/2002 | Foley et al. |
| 2002/0198532 A1 | 12/2002 | Michelson |
| 2003/0065396 A1 | 4/2003 | Michelson |
| 2003/0074063 A1 * | 4/2003 | Gerbec ................. A61F 2/4611 |
| | | 623/16.11 |
| 2003/0074064 A1 | 4/2003 | Gerbec et al. |
| 2003/0171812 A1 | 9/2003 | Grunberg et al. |
| 2003/0220650 A1 | 11/2003 | Major et al. |
| 2003/0236520 A1 | 12/2003 | Lim et al. |
| 2004/0073308 A1 | 4/2004 | Kuslich et al. |
| 2004/0087947 A1 | 5/2004 | Lim et al. |
| 2004/0087994 A1 | 5/2004 | Suddaby |
| 2004/0102774 A1 | 5/2004 | Trieu |
| 2004/0133280 A1 | 7/2004 | Trieu |
| 2004/0143827 A1 | 7/2004 | de Jong |
| 2004/0167625 A1 | 8/2004 | Beyar et al. |
| 2004/0210231 A1 | 10/2004 | Boucher et al. |
| 2004/0215343 A1 | 10/2004 | Hochschuler et al. |
| 2004/0236342 A1 | 11/2004 | Ferree et al. |
| 2005/0070911 A1 * | 3/2005 | Garrison .............. A61B 17/885 |
| | | 606/90 |
| 2005/0107600 A1 | 5/2005 | Frankel et al. |
| 2005/0107800 A1 | 5/2005 | Frankel et al. |
| 2005/0143827 A1 | 6/2005 | Globerman et al. |
| 2005/0182416 A1 | 8/2005 | Lim et al. |
| 2005/0222681 A1 | 10/2005 | Richley et al. |
| 2005/0228391 A1 | 10/2005 | Levy et al. |
| 2005/0234493 A1 | 10/2005 | Carr et al. |
| 2005/0261781 A1 | 11/2005 | Sennett et al. |
| 2005/0273135 A1 | 12/2005 | Chanduszko et al. |
| 2005/0278036 A1 | 12/2005 | Leonard et al. |
| 2006/0004455 A1 | 1/2006 | Leonard et al. |
| 2006/0085070 A1 | 4/2006 | Kim |
| 2006/0116689 A1 | 6/2006 | Albans et al. |
| 2006/0129101 A1 | 6/2006 | McGuckin |
| 2006/0149268 A1 | 7/2006 | Truckai et al. |
| 2006/0149379 A1 | 7/2006 | Kuslich et al. |
| 2006/0184192 A1 | 8/2006 | Markworth et al. |
| 2006/0235423 A1 | 10/2006 | Cantu |
| 2006/0241644 A1 | 10/2006 | Osorio et al. |
| 2006/0271049 A1 | 11/2006 | Zucherman et al. |
| 2006/0281595 A1 | 12/2006 | Narita et al. |
| 2007/0016303 A1 | 1/2007 | Jackson |
| 2007/0021836 A1 | 1/2007 | Doty |
| 2007/0032790 A1 | 2/2007 | Aschmann et al. |
| 2007/0032791 A1 | 2/2007 | Greenhalgh |
| 2007/0055201 A1 | 3/2007 | Seto et al. |
| 2007/0093899 A1 | 4/2007 | Dutoit et al. |
| 2007/0142915 A1 | 6/2007 | Altarac et al. |
| 2007/0149978 A1 | 6/2007 | Shezifi et al. |
| 2007/0173826 A1 | 7/2007 | Canaveral et al. |
| 2007/0173832 A1 | 7/2007 | Tebbe et al. |
| 2007/0173939 A1 | 7/2007 | Kim et al. |
| 2007/0225705 A1 | 9/2007 | Osorio et al. |
| 2007/0260315 A1 | 11/2007 | Foley et al. |
| 2008/0051894 A1 | 2/2008 | Malandain et al. |
| 2008/0058823 A1 | 3/2008 | Reiley et al. |
| 2008/0065087 A1 | 3/2008 | Osorio et al. |
| 2008/0065089 A1 | 3/2008 | Osorio et al. |
| 2008/0086133 A1 | 4/2008 | Kuslich et al. |
| 2008/0114367 A1 | 5/2008 | Meyer |
| 2008/0125784 A1 | 5/2008 | Rabiner et al. |
| 2008/0140079 A1 | 6/2008 | Osorio et al. |
| 2008/0140207 A1 | 6/2008 | Olmos et al. |
| 2008/0147193 A1 | 6/2008 | Matthis et al. |
| 2008/0167657 A1 | 7/2008 | Greenhalgh |
| 2008/0183204 A1 | 7/2008 | Greenhalgh et al. |
| 2008/0269766 A1 | 10/2008 | Justis |
| 2008/0280712 A1 | 11/2008 | Ryouno et al. |
| 2009/0005782 A1 | 1/2009 | Chirico et al. |
| 2009/0005821 A1 | 1/2009 | Chirico |
| 2009/0171390 A1 | 7/2009 | Sankaran |
| 2009/0204216 A1 | 8/2009 | Biedermann et al. |
| 2009/0228012 A1 | 9/2009 | Gangji et al. |
| 2009/0234398 A1 | 9/2009 | Chirico et al. |
| 2009/0264927 A1 | 10/2009 | Ginsberg et al. |
| 2009/0276048 A1 | 11/2009 | Chirico et al. |
| 2009/0281628 A1 | 11/2009 | Oglaza et al. |
| 2009/0292323 A1 | 11/2009 | Chirico et al. |
| 2009/0299378 A1 | 12/2009 | Knopp |
| 2009/0306715 A1 | 12/2009 | Jackson et al. |
| 2009/0326581 A1 | 12/2009 | Galley |
| 2010/0069913 A1 | 3/2010 | Chirico et al. |
| 2010/0070035 A1 | 3/2010 | Mayer |
| 2010/0185291 A1 | 7/2010 | Jimenez et al. |
| 2010/0324607 A1 | 12/2010 | Davis |
| 2011/0021298 A1 | 1/2011 | Kurematsu et al. |
| 2011/0032020 A1 | 2/2011 | Campbell et al. |
| 2011/0046739 A1 | 2/2011 | Oglaza et al. |
| 2011/0066186 A1 | 3/2011 | Boyer, II et al. |
| 2011/0130232 A1 | 6/2011 | Barrette et al. |
| 2012/0071977 A1 | 3/2012 | Oglaza et al. |
| 2012/0123481 A1 | 5/2012 | Lin |
| 2012/0150228 A1 | 6/2012 | Zappacosta et al. |
| 2014/0031940 A1 | 1/2014 | Banouskou |
| 2014/0114368 A1 | 4/2014 | Lin et al. |
| 2014/0135780 A1 | 5/2014 | Lee et al. |
| 2015/0250518 A1 | 9/2015 | Chirico et al. |
| 2016/0157898 A1 | 6/2016 | Fuerderer |
| 2017/0000622 A1 | 1/2017 | Thommen et al. |

FOREIGN PATENT DOCUMENTS

| | | |
|---|---|---|
| CN | 1713863 A | 12/2005 |
| CN | 1830399 A | 9/2006 |
| CN | 101031259 A | 9/2007 |
| CN | 101530343 A | 9/2009 |
| CN | 102427769 A | 4/2012 |
| CN | 103211669 A | 7/2013 |
| DE | 20017962 U1 | 1/2001 |
| DE | 20303642 U1 | 4/2003 |
| EP | 0567424 A1 | 10/1993 |
| EP | 0571555 A1 | 12/1993 |
| EP | 0796593 A2 | 9/1997 |
| EP | 1778136 A2 | 5/2007 |
| EP | 2074956 A1 | 7/2009 |
| FR | 2782632 A1 | 3/2000 |
| FR | 2796268 A1 | 1/2001 |
| GB | 2435292 A | 8/2007 |
| GB | 2436292 A | 9/2007 |
| JP | S62054313 A | 3/1987 |
| JP | 2000070274 A | 3/2000 |
| JP | 2001173863 A | 6/2001 |
| JP | 2002535066 A | 10/2002 |
| JP | 2006507090 A | 3/2006 |
| JP | 2008501462 A | 1/2008 |

(56) References Cited

FOREIGN PATENT DOCUMENTS

| | | |
|---|---|---|
| JP | 2009160399 A | 7/2009 |
| JP | 2013078639 A | 5/2013 |
| KR | 20070068338 A | 6/2007 |
| RU | 2070006 C1 | 12/1996 |
| TW | I318110 B | 12/2009 |
| WO | 9730666 A2 | 8/1997 |
| WO | 9834568 A1 | 8/1998 |
| WO | 9902214 A1 | 1/1999 |
| WO | 1999021501 A1 | 5/1999 |
| WO | 9952447 A1 | 10/1999 |
| WO | 0044319 A1 | 8/2000 |
| WO | 0049978 A1 | 8/2000 |
| WO | 0078253 A1 | 12/2000 |
| WO | 0101895 A1 | 1/2001 |
| WO | 01060263 A1 | 8/2001 |
| WO | 200154598 A1 | 8/2001 |
| WO | 0166047 A1 | 9/2001 |
| WO | 200176492 A1 | 10/2001 |
| WO | 0230338 A1 | 4/2002 |
| WO | 03003951 A1 | 1/2003 |
| WO | 2004000166 A2 | 12/2003 |
| WO | 2004019756 A2 | 3/2004 |
| WO | 2004034924 A3 | 6/2004 |
| WO | 2004047689 A1 | 6/2004 |
| WO | 2004026188 A3 | 10/2004 |
| WO | 2004086934 A3 | 11/2004 |
| WO | 2005048856 A1 | 6/2005 |
| WO | 2005120400 A3 | 4/2006 |
| WO | 2006042206 A2 | 4/2006 |
| WO | 2006068682 A1 | 6/2006 |
| WO | 2006116760 A2 | 11/2006 |
| WO | 2007075768 A2 | 7/2007 |
| WO | 2007075788 A2 | 7/2007 |
| WO | 2007076308 A2 | 7/2007 |
| WO | 2007079237 A2 | 7/2007 |
| WO | 2007084239 A2 | 7/2007 |
| WO | 2007076374 A3 | 12/2007 |
| WO | 2007073488 A3 | 4/2008 |
| WO | 2007041665 A3 | 7/2008 |
| WO | 2007076376 A3 | 12/2008 |
| WO | 2009005851 A1 | 1/2009 |
| WO | 2009037509 A1 | 3/2009 |
| WO | 2009094009 A1 | 7/2009 |
| WO | 2009100200 A1 | 8/2009 |
| WO | 2009125243 A1 | 10/2009 |
| WO | 2010100287 A1 | 9/2010 |
| WO | 2010103344 A1 | 9/2010 |

OTHER PUBLICATIONS

Chinese Search Report for Application No. CN200980159243.7 dated Apr. 8, 2014.
Chinese Search Report for Application No. CN200980159243.7 dated Oct. 27, 2014.
Chinese Search Report for Application No. CN200980159243.7 dated Sep. 22, 2013.
Chinese Search Report for Application No. CN2011800714364 dated May 13, 2016.
Chinese Search Report for Application No. CN201310319755.3 dated May 6, 2015.
English language abstract for JP 2000-070274 extracted from espacenet.com database on Jan. 23, 2019, 2 pages.
English language abstract for JP 2002-535066 extracted from espacenet.com database on Jan. 23, 2019, 2 pages.
European Search Report dated Feb. 22, 2013 for EP Application No. 12191848.6, filed Jun. 8, 2005.
French Preliminary Search Report corresponding to French Patent Application No. 0406211 dated Feb. 15, 2005.
French Preliminary Search Report corresponding to French Patent Application No. 05 05798 dated Oct. 28, 2005.
French Preliminary Search Report for Application No. FR1363467 dated Sep. 24, 2014.
International Preliminary Report on Patentability dated Dec. 14, 2006 for PCT/IB2005/002631, filed Jun. 8, 2005.
International Preliminary Report on Patentability dated Oct. 12, 2010 for PCT/IB2008/002246, filed Apr. 8, 2008.
International Preliminary Report on Patentability dated Oct. 6, 2013 for PCT/IB2011/001480, filed Apr. 7, 2011.
International Preliminary Report on Patentability dated Oct. 8, 2013 for PCT/IB2011/001480, filed Apr, 7, 2011.
International Preliminary Report on Patentability dated Sep. 13, 2011 for PCT/IB2009/005385, filed Mar. 12, 2009.
International Search Report and Written Opinion of the International Searching Authority corresponding to International PCT/IB2005/002631 dated Feb. 7, 2006.
International Search Report and Written Opinion, dated Feb. 25, 2015 for International Application No. PCT/FR2014/053549, filed Dec. 23, 2014, and English translations of the International Search Report and Written Opinion.
International Search Report dated Dec. 12, 2009 and Written Opinion for PCT/IB2009/005385, filed Mar. 12, 2009.
International Search Report dated Dec. 6, 2011 for PCT/IB2011/001480, filed Apr. 7, 2011.
International Search Report dated Jan. 29, 2009 for Application No. PCT/IB2008/002246, filed Apr. 8, 2008.
International Search Report for Application No. PCT/US2009/033192 dated Mar. 19, 2009.
Kuslich et al., U.S. Appl. No. 60/219,853, filed Jul. 21, 2000, titled "Expandable porous mesh bag device for reduction, filling,fixation and supporting of bone".
Russian Search Report for RU2011141272 dated Feb. 8, 2013.
Supplementary Search Report dated Apr. 8, 2014, by the State Intellectual Property Office of the People's Rep. of China for Application No. 200980159243.7, filed Mar. 12, 2009.
Taiwanese Search Report for Application No. TW099106921 dated Mar. 12, 2009.
Taiwanese Search Report for Application No. TW101112279 dated Apr. 7, 2011.

* cited by examiner

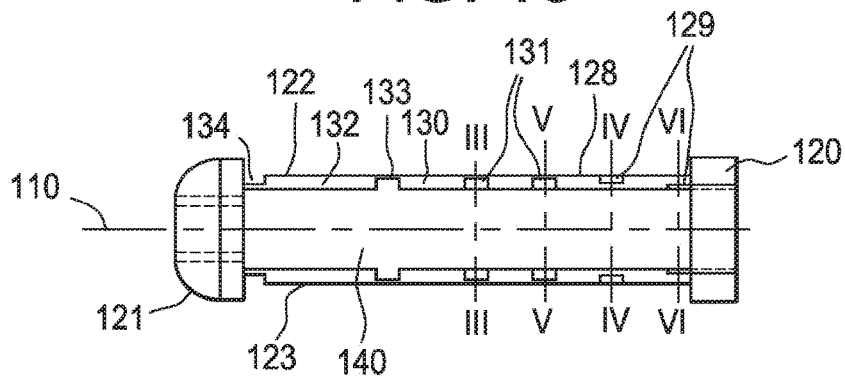
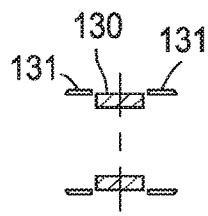 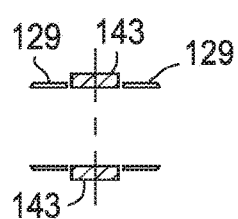 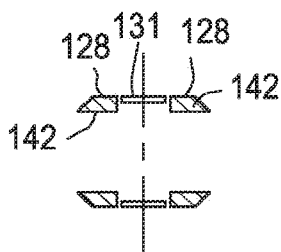 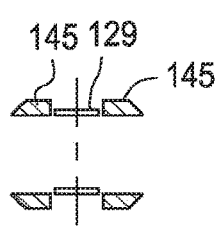
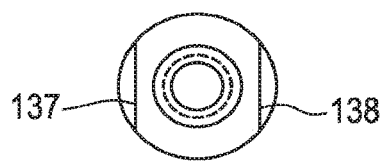
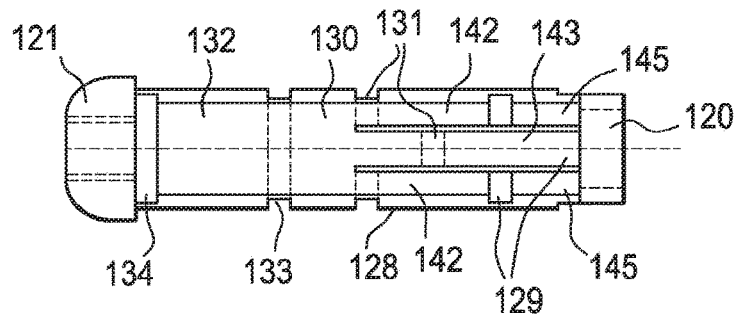

SYSTEMS AND IMPLANTS FOR BONE RESTORATION

PRIORITY CLAIM

This is a continuation of co-pending U.S. application Ser. No. 16/126,371, filed Sep. 10, 2018, which is a continuation of U.S. application Ser. No. 15/194,440, filed Jun. 27, 2016, now U.S. Pat. No. 10,098,751, which is a continuation of U.S. patent application Ser. No. 12/938,993, filed Nov. 3, 2010, now U.S. Pat. No. 9,408,707, which is a continuation of U.S. patent application Ser. No. 11/150,676, filed Jun. 9, 2005, now U.S. Pat. No. 7,846,206, which is a continuation-in-part of U.S. patent application Ser. No. 10/951,766, filed Sep. 29, 2004, now abandoned, which claims priority to French Patent Application No. 04 06211 filed on Jun. 9, 2004. The entire disclosures of the above applications are incorporated herein by reference.

FIELD OF THE INVENTION

The present invention relates to the field of surgery and medical implants and more particularly to devices and methods for restoring human or animal bone anatomy using medical bone implants.

BACKGROUND OF INVENTION

Various causes can be at the root of bone compression, in particular osteoporosis which causes (for example) natural vertebral compression under the weight of the individual, but also traumas, with the two causes occasionally being combined. Such bone compressions can affect the vertebrae but also concern other bones, such as the radius and the femur, for example.

Several vertebroplasty techniques are known for effecting a vertebral correction i.e., to restore a vertebra to its original shape, or a shape similar to the latter. For example, one technique includes the introduction of an inflatable balloon into a vertebra, then introducing a fluid under pressure into the balloon in order to force the cortical shell of the vertebra, and in particular the lower and upper vertebral plateaus, to correct the shape of the vertebra under the effect of the pressure. This technique is known by as kyphoplasty. Once the osseous cortical shell has been corrected, the balloon is then deflated, and withdrawn from the vertebra in order to be able to inject a cement into the cortical shell which is intended to impart, sufficient mechanical resistance for the correction to have a significant duration in time.

A notable disadvantage of the kyphoplasty method resides in its numerous manipulations, in particular inflation, and in the necessity to withdraw the balloon from the patient's body. Furthermore, the expansion of a balloon is poorly controlled because the balloon's volume is multi-directional, which often causes a large pressure to be placed on the cortical shell in unsuitable directions. Such large pressures risk bursting of the cortical shell, and in particular, the lateral part of the cortical shell connecting the lower and upper plateaus of a vertebra.

Other vertebral implants exist which are intended to fill a cavity in a vertebra. Such implants, however, generally adopt a radial expansion principle obtained by formation of a plurality of points which stand normally to the longitudinal axis of the implant under the effect of contraction of the latter. Such implants impose too high a pressure on individual points which may pierce the material on which the points support. Furthermore, similar to kyphoplasty, very high pressure can cause bursting of the tissues or organ walls, such as the cortical shell, for example. Furthermore, the radial expansion of some implants does not allow a particular expansion direction to be favoured.

SUMMARY

Embodiments of the present invention reduce the above noted disadvantages and provide additional advantages over the prior art devices of bone restoration. More particularly, some embodiments of the present invention include methods for restoration of human or animal bone anatomy, and include one or more of the following steps:

introduction, into a bone for restoring, of an expansible implant according to a single determined expansion plane which is preferably intrinsic to the implant, positioning the expansible implant in the bone in order to make the expansion plane correspond with a bone restoration plane, opening out the expansible implant in the bone restoration plane, and injecting a filling material in an around the implant.

The method, according to some embodiments of the invention, allows the creation of a reinforced structure resulting in a solid structure (i.e., the implant incorporated by a hardened filling material thanks to the expansion of the implant). Moreover, the filling material can be injected under relatively low pressure since the implant remains in place which enables the preservation of the dimensions of the corrected bone structure.

It is another feature of an embodiment of the present invention that the expansible implant may be expanded/opened-out in the bone restoration plane to a determined value: between a minimum thickness of the implant before any expansion and a maximum thickness of the implant after maximum expansion. Such a feature allows the expansion value of the implant to be controlled, for example, for a given vertebral correction.

Another advantageous feature of an embodiment of the present invention includes the opening out of the expansible implant, by opening out first and second opposite plates, forming (respectively) first and a second support surfaces for the bone. Such a feature allows the pressure which is exerted by the implant on the tissues in contact with the latter to be reduced, by increasing the contact or support surface on the tissues.

The length of the implant may also be sized to be substantially equal to at least one of the first and second support surfaces in the bone. Such a feature allows optimization of a ratio of the support length on the tissues to the length of the implant. For example, the closer this ratio is to one, the more the implant will be usable in places requiring a small length. Moreover, this feature also allows the introduction of a filling material with low injection pressure—in one embodiment, the injection pressure is the lowest possible so as to avoid having the filling material be injected into inappropriate tissues such as blood vessel walls (for example).

In another embodiment of the invention, each of the first and second plates may form partially cylindrical support surfaces, one portion of which may be parallel to a longitudinal axis of the expansible implant.

In another embodiment of the present invention, the opening out first and second plates includes raising the latter using one or more supports under the plates. Such a feature allows a ratio of the length of the support surfaces to the length of the implant to be increased to be as close to one (1)

as possible, as will be explained in more detail further on with the description of an embodiment of the invention. Furthermore, this feature allows thrust forces to be distributed under the plate in order to reduce the cantilever.

A filler cement may be injected in an around the implant, so as to aid in compressive load with the implant in bone restoration. Cements that may be used with the implants according to the disclosed embodiments may include an ionic cement, in particular a phosphocalcic cement, an acrylic cement or a compound of the latter. Accordingly, the combination of the implant and the cement is not unlike a steel reinforced concrete structure in the construction of buildings.

In one embodiment of the present invention, an expansible implant for bone restoration is presented and may include a single plane of expansion intrinsic to the implant, where upon the single plane of expansion corresponds to a bone restoration plane and first and second opposed plates respectively form first and a second bearing surfaces for the bone. The first and second plates are intended to move away one from the other according to the single plane of expansion at the time of the expansion of the implant. The implant may also include first and second supports for each of the first and second bearing surfaces, located under each plate respectively and means for controlling expansion of the implant. The controlling means may include a material web provided between each support and a corresponding plate, having a determined thickness which controls expansion of the implant. Moreover, one or more implants may be used in a single bone to produce a more symmetrical bone restoration (see FIG. 37).

Accordingly, additional embodiments of the present invention may also include control means for controlling a determined expansion value, between a minimum thickness of the implant before any expansion of the latter and a maximum thickness of the implant after its maximum expansion.

The implant may also preferably include a means for positioning the expansible implant in bone in order to make the expansion plane of the implant correspond substantially with a bone restoration plane. Such means may include an engagement means allowing angular orientation of the implant about the longitudinal axis, including flat surfaces for attachment with an implant carrier, and threaded engagement.

Another embodiment of the invention is directed to a system for bone restoration and may include at least one expansible implant having a single plane of expansion for corresponding to a bone restoration plane, a first tube for positioning adjacent an exterior surface of a bone for restoration, and a first rod having a threaded end for affixing into a distal end of the interior of the bone, where the first rod being received within the first tube. The system may also include a second tube for receiving the first tube therein and a third tube for receiving the second tube, where the third tube including one or more engagement members for anchoring the third tube on the exterior surface of the bone. The system may further include a drill for establishing an enlarged opening in the side of the bone, where the drill is guided by the first rod and a medical insertion device for inserting an expansible implant into a patient.

Another embodiment of the invention is directed to a medical insertion device for inserting an expansible implant into a patient. The device may include a gripping portion having a central bore, a first tube housed in the central bore, a threaded rod housed in the first tube having a distal end for receiving an implant for insertion into the patient, a handle attached to the gripping portion and/or the implant carrier, and a gauge for determining an expansion of the implant.

Still other features, advantages, embodiments and objects of the present invention will become even more clear with reference to the attached drawings, a brief description of which is set out below, and the following detailed description.

BRIEF DESCRIPTION OF THE FIGURES

FIG. 10 illustrates a lateral view of the example according to FIG. 8.

FIG. 11 illustrates a view in section according to the line of FIG. 10.

FIG. 12 illustrates a view in section according to the line IV-IV of FIG. 10.

FIG. 13 illustrates a view in section according to the line V-V of FIG. 10.

FIG. 14 illustrates a view in section according to the line VI-VI of FIG. 10.

FIG. 15 illustrates an end view according to direction G of the example according to FIG. 8.

FIG. 16 illustrates a view from above of the example according to FIG. 8.

DETAILED DESCRIPTION

Figure 1A:
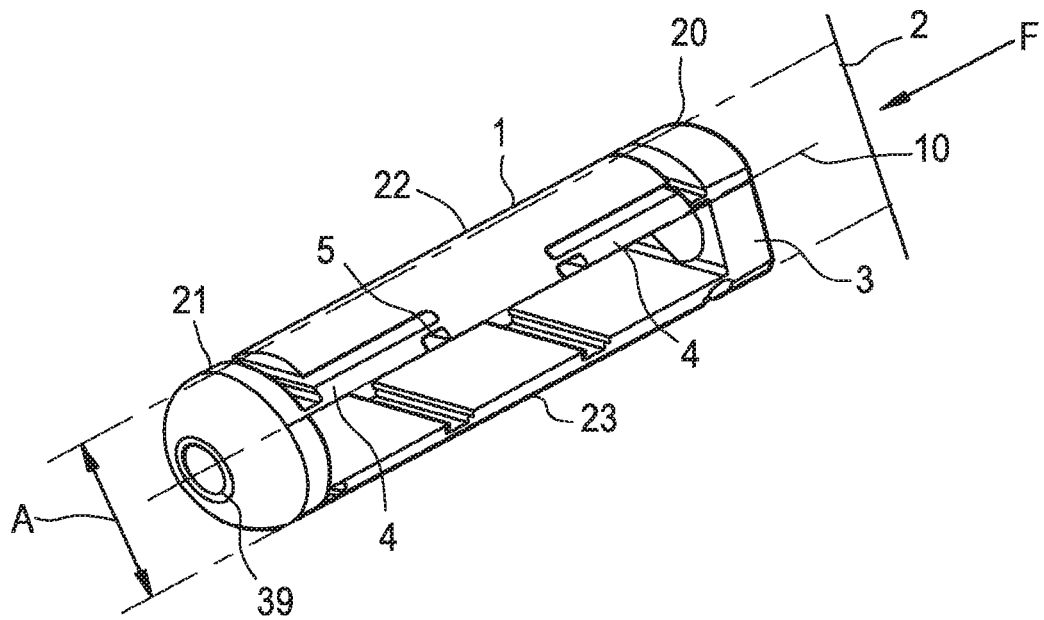
FIG. 1A illustrates a perspective view of one embodiment of an expansible implant according to the invention, in a resting position.

The expansible implant 1 represented in FIGS. 1A to 7 may include one or more of the following:

a single determined expansion plane 2, which may be intrinsic to the implant, means 3 for positioning the expansible implant in the bone allowing the expansion plane to correspond with a bone restoration plane, means 4 for opening out the expansible implant in the single expansion plane 2 means 5 for controlling a determined expansion value, between a minimum thickness A of the implant before any expansion of the latter and a maximum thickness B of the implant after its maximum expansion, and a first 6 and a second 7 opposite plate which are able to form respectively a first 8 and a second 9 support surface in the bone intended to be moved apart one from the other along the single expansion plane 2 during expansion of the implant 1.

Figure 1B:
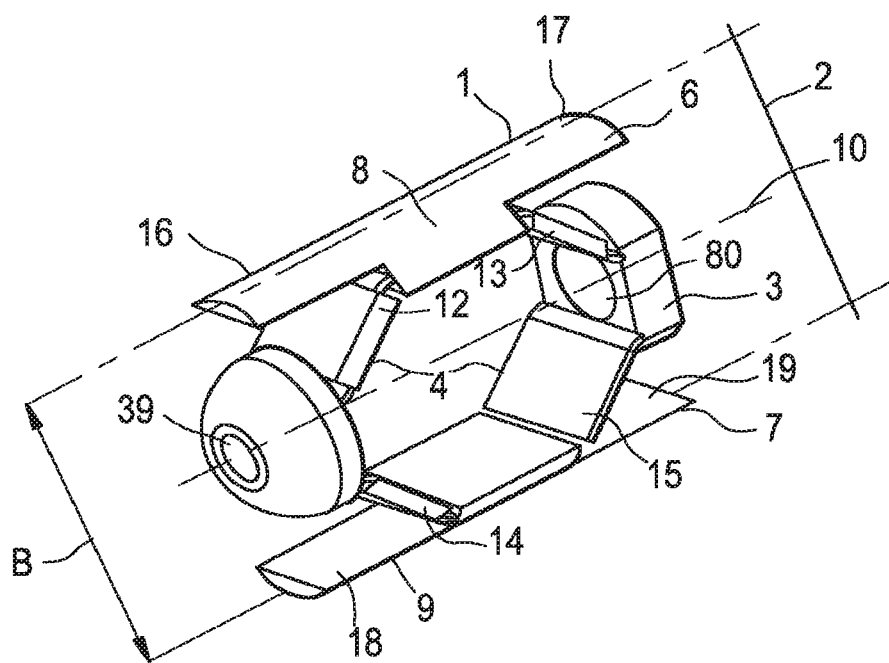
FIG. 1B illustrates the example of FIG. 1A, in opened-out position.

As shown in FIGS. 1A and 1B, implant 1 may include a cylindrical shape with a transverse circular exterior section, and can be manufactured of biocompatible material, for example titanium, into a tubular body using lathe, laser, and/or electro-erosion manufacturing techniques (cast manufacturing may also be used). The implant 1 may also include a first end 20 and a second end 21, each respectfully adopting the shape of a transverse section of the tubular body. The ends are preferably intended to be brought towards one another to allow the opening-out/expansion of the implant, as represented in FIGS. 1B and 2B. Accordingly, the two ends 20, 21 are connected to each other by a first 22 (which also may be referred to as "upper" arm) and second 23 (which also may be referred to as "lower" arm) rectilinear arm, which are parallel when the implant is not opened out and formed longitudinally in the tubular body, and are able to be folded under the first 6 and second 7 opposite plates as an the effect of bringing the ends 20 and 21 one towards the other, while also distancing the first 6 and second 7 opposite plates from the longitudinal axis 10 of the tubular body.

Figure 2A:
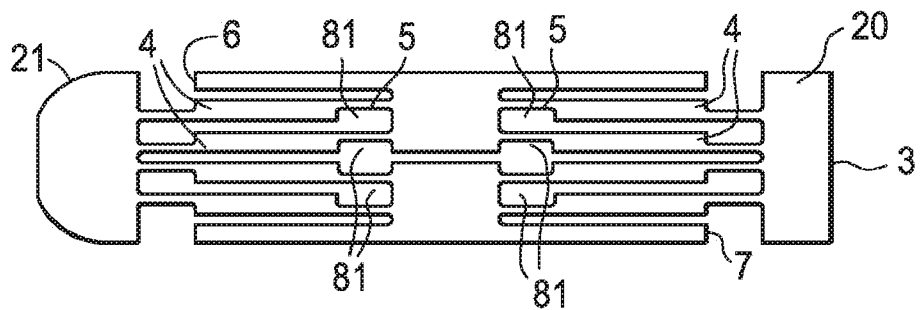
FIG. 2A illustrates a side view of another embodiment of an expansible implant according to the invention, in a resting position.
Figure 2B:
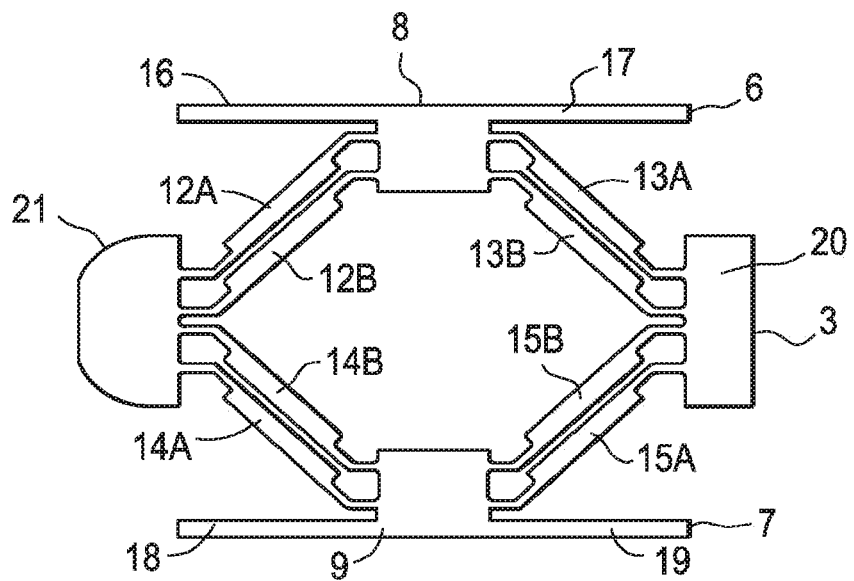
FIG. 2B illustrates the example of FIG. 2A, in opened-out position.
Figure 2C:
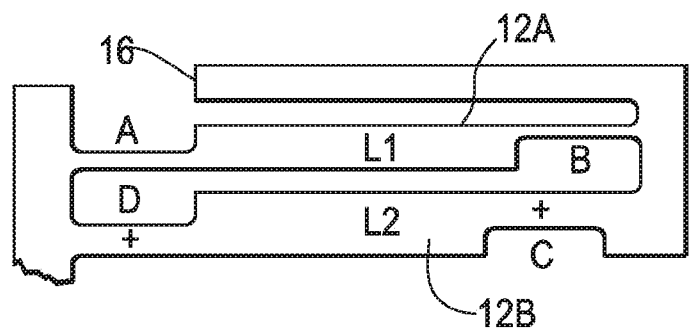
FIG. 2C illustrates an enlarged side view of the support members for the embodiment illustrated in FIGS. 2A and 2B.
Figure 3:
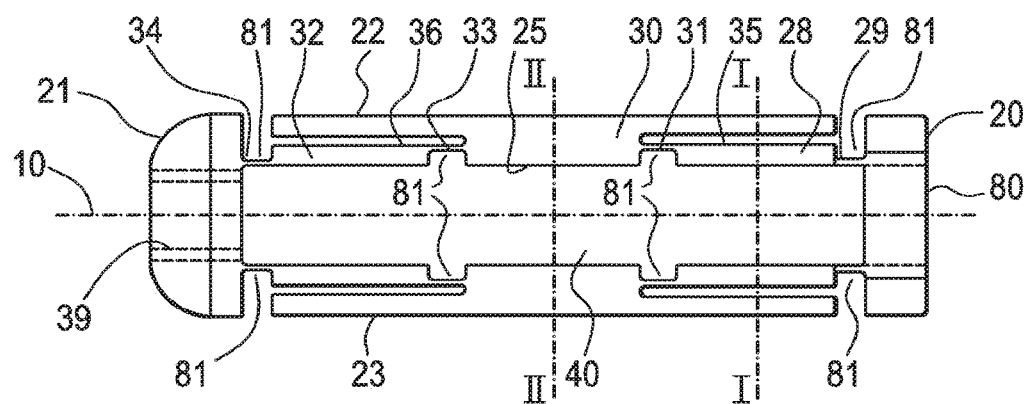
FIG. 3 illustrates a lateral view of the example according to FIG. 1A.

FIGS. 2A-2C illustrate an embodiment of the implant which is similar to the embodiment disclosed in FIGS. 1A and 1B, but with an additional set of supports (e.g., a four bar linkage). More specifically, the implant in FIGS. 2A-2C includes supports 12A, 13B, 13A, 13B, 14A, 14B, 15A, and 15B. The additional supports may provide further rigidity for the implant and/or may insure that plates 6 and 7 open-out in a substantially parallel and/or even manner.

Figure 4:
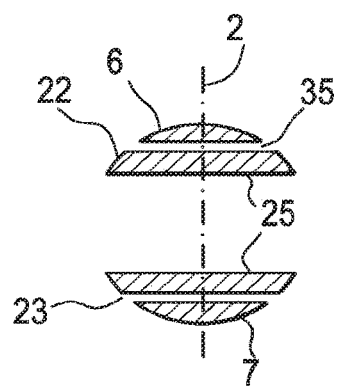
FIG. 4 illustrates a view in section according to the line I-I of FIG. 3.
Figure 5:
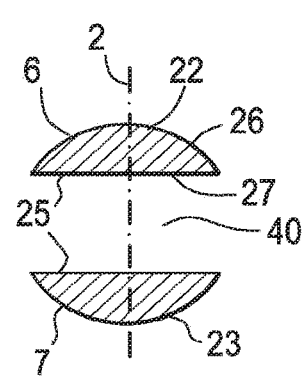
FIG. 5 illustrates a view in section according to the line II-II of FIG. 3.
Figure 6:
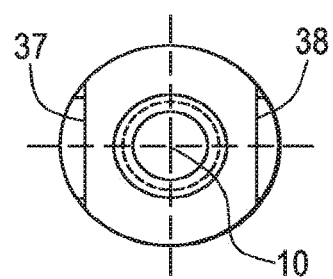
FIG. 6 represents an end view according to view F of the example according to FIG. 1A.
Figure 7:
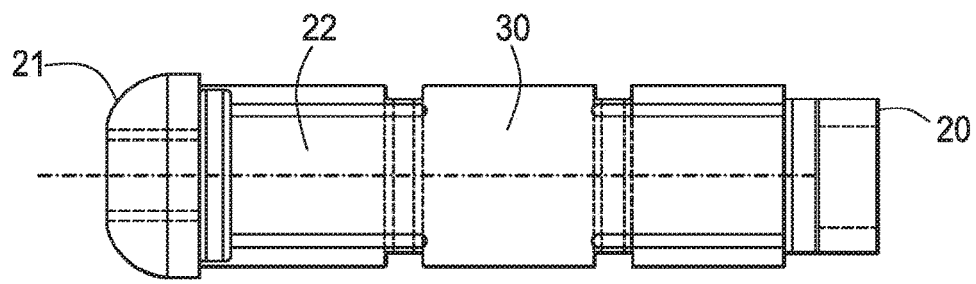
FIG. 7 illustrates a view from above of the example according to FIG. 1A.
Figure 8:
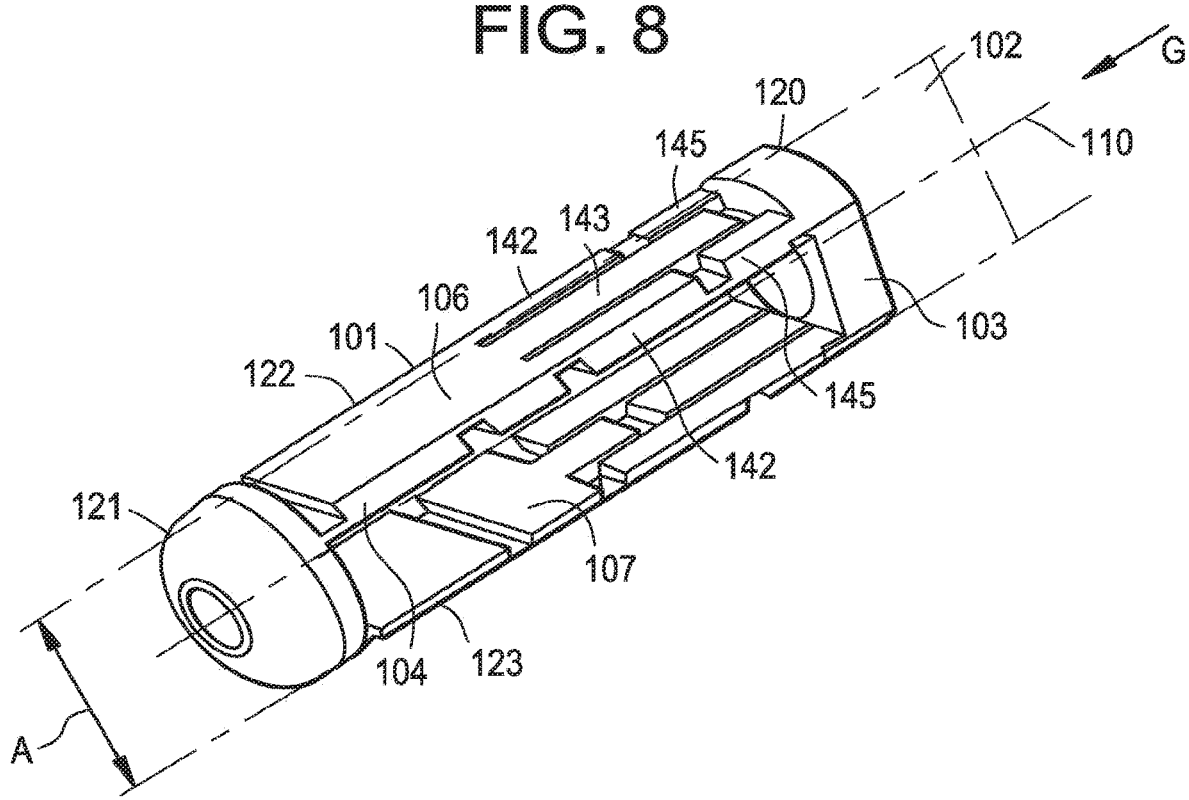
FIG. 8 illustrates a perspective view of another embodiment of an expansible implant according to the invention, in a resting position.

As represented in FIGS. 4-5, in order to allow the arms 22 and 23 to be opened out in a single expansion plane 2 (passing through the longitudinal axis 10 of the tubular body), the arms 22 and 23 are preferably diametrically opposed. In that regard, the arms 22, 23 may be formed from a transverse recess 40 of the tubular body, traversing the tubular body throughout, and extending over the length of the tubular body between the two ends 20 and 21 of the implant 1. As represented in FIG. 5, the arms, 22, 23 connecting the two ends 20 and 21, respectively adopt a transverse section bounded by a circular arc 26 of the exterior surface of the tubular body. Chord 27 defines the circular arc 26 and may be included in the wall 25 to form recess 40. The recess 40 may be symmetrical with respect to the longitudinal axis 10.

Each arm 22, 23 may be divided into three successive rigid parts, which may be articulated together in conjunction with the ends 20 and 21 as follows. With respect to the upper arm 22: a first rigid part 28 is connected at one end to end 20 by means of an articulation 29. The other end of rigid part 28 is connected to a first end of a second, adjacent, central rigid part 30 by means of an articulation 31. The second rigid part 30 may be connected at a second end to the third rigid part 32 by means of an articulation 33. The other end of the third rigid part 32 may be connected to end 21 by means of an articulation 34. Preferably, the articulations 29, 31, 33 and 34 may include one degree of freedom in rotation, acting, respectively, about axes which are perpendicular to the expansion plane 2. Preferably, articulations 29, 31, 33 and 34 are formed by a thinning of the wall forming the arm in the relevant articulation zone, as represented in FIGS. 1A-3 (see also, e.g., reference numerals 5 and 81).

Each arm 22, 23 opens out such that the central rigid part 30 moves away from the longitudinal axis 10 of the implant pushed by the two adjacent rigid parts 28 and 32, when the ends 20 and 21 of the implant are brought one towards the other. As represented more particularly in FIG. 3, in order to initiate the movement of the arm in the correct direction when the ends 20 and 21 are brought towards the other, it is preferable to establish a suitable rotation couple of the various parts of the arm.

Accordingly, ends of rigid parts 28, 32 of upper arm 22 may be articulated with ends 20 and 21, respectively, via a material web formed on the rigid parts. Other ends of rigid parts 28, 32 may also be articulated with the central rigid part 30 via a material web formed on rigid parts 28, 32. The displacement of the articulations establish a rotation couple on the rigid parts 28 and 32 when a force is applied to bring the ends 20 and 21 together along the longitudinal axis 10 of the implant. This displacement tends to make the rigid part 32 pivot towards the exterior of the implant as a result of moving the central rigid part 30 away from the longitudinal axis 10.

The lower arm 23 may be constructed in a similar manner as the upper arm and is preferably symmetrical to the upper arm 22 with respect to a plane which is perpendicular to the expansion plane 2 passing through the longitudinal axis 10.

Thus, according to some embodiments of the present invention, the articulations between the upper 22 and lower 23 arms and corresponding rigid parts are preferably formed by weakened zones produced by grooves 81. The grooves define a thin web of material (i.e., material web) formed from the tubular body, the thickness of which may be determined by the depth of the grooves 81 (as represented in the figures) in order to allow plastic deformation of the material without breaking. Specifically, the rigid parts 28 and 32 of the upper arm 22, and their symmetrical ones on the lower arm 23, can adopt a position, termed extreme expansion, in which the intended rigid parts are perpendicular to the longitudinal axis 10 of the implant 1, when the ends 20 and 21 are brought one towards the other such that the latter is opened up until its maximum expansion capacity, resulting in plastic deformation of the corresponding material. The width of the grooves 81 are preferably pre-determined to allow such a clearance of the parts of the upper and lower arms and also to impart a suitable radius of curvature to the webs in order to ensure plastic deformation without rupture of the material.

The first 6 and second 7 opposite plates may be formed in the upper 22 and lower 23 arms. With respect to the upper arm 22, for example, plate 6 may be formed by the central rigid part 30 and by material extensions (rigid parts 28 and 32) extending out both sides thereof. In order to produce the plate 6, rigid parts 28 and 32 are separated from the upper arm 22 using a pair of transverse slots 35 and 36 which extend longitudinally over the length each respective end part (see FIGS. 3-4). Articulations 31 and 33 and rigid parts 28 and 32 form, respectively, a first 12 and a second 13 support (FIG. 1B) for the first 6 plate. The same applies to the second plate 7 by symmetry.

Hence, the first 6 and second 7 plates may comprise respectively a first 16, 18 and a second 17, 19 cantilever wing, the respective attachment zones of which are situated at the level of the first 12, 14 and second 13, 15 supports. As represented in FIGS. 1A-B, the first 16, 18 and second 17, 19 cantilever wings may include a length corresponding substantially to the maximum displacement value of one of the first 6 or second 7 plates in the single expansion plane 2.

The first 6 and second 7 plates form first 8 and second 9 support surfaces, respectively, each having a length which may be substantially equal to the length of the implant and which may be displaced perpendicularly to the longitudinal axis 10 during expansion. According to one embodiment of the invention, since the implant 1 is formed in a tubular body, the first 6 and second 7 plates form, respectively, curved support surfaces, which are preferably parallel to the longitudinal axis 10.

The means 3 for positioning the expansible implant in a bone which allow the expansion plane 2 to correspond with a bone restoration plane, may include an engagement means which allows for the angular orientation of the implant about longitudinal axis 10. For example, such means may include flat surfaces 37, 38 which are formed on the cylindrical surface with a circular section of end 20, which may allow for rotational engagement of the implant 1.

The means 4 for opening out the expansible implant in a single expansion plane 2, may include rigid parts 28 and 32 of upper arm 22 and the corresponding symmetrical rigid parts on the lower arm 23, allowing opening out of the first 6 and second 7 plates. An implant carrier 71 (see FIG. 23) may be used to allow the ends 20 and 21 of the implant to be brought together when placed within the bone. The implant carrier 71, by being supported on the end 20, for example, allows the end 21 to be pulled toward end 20, or by being supported on end 21, end 20 is pushed toward end 21. To this end, the distal end 21, for example, comprises an opening/distal orifice 39 threaded along the longitudinal axis 10 in order to allow the engagement of the implant carrier 71, which includes a corresponding threaded portion. The proximal end 20 may include a bore 80 along the longitudinal axis 10 in order to allow the passage of a core of the implant carrier 71 as will be explained further on.

A control means may be provided by the implant carrier which may include a millimetric control means for bringing ends 20 and 21 together, preferably by means of screw-thread engagement, allowing the expansion to be stopped at any moment as a function of requirements. On the other hand, control means 5 provided by the articulations of the arms 22 and 23, more specifically, by the thickness of the material webs defining each arm which, deforming in the plastic region, allow the expansion to substantially preserve a determined opening-up position of the arms, apart from elastic shrinkage which is negligible in practice.

The expansion of the plates 6 and 7 of the implant, and their stabilisation once opened up, can be achieved through adaptation of plates 6 and 7 to the bone geometry by the plates. Specifically, in some embodiments of the invention, the implant 1 allows a non-parallel displacement of plates 6 and 7 and, at the end of the displacement, allows a definitive position of the plates in a non-parallel state if necessary (e.g., as a function of the bone anatomy). For example, the expansion of plates 6 and 7 may be non-parallel if the lengths of individual support arms are different. For example, if supports 12 and 14 are longer than supports 13 and 15 (see FIGS. 1A-2B), opening out the implant will force plates 6 and 7 to angle away from each other. In FIGS. 1A-2B, this would result that plates 6 and 7 at end 21 to be further apart one another then at end 20. As one of ordinary skill in the art will appreciate, depending upon the configuration, only one respective support need be lengthened/shortened, to obtain a particular angle.

Similarly, as shown in FIGS. 2A-2C, when the four bar linkage comprising supports 12A, 12B, 13A, 13B, 14A, 14B, 15A, 15B, as shown, are equal lengths (i.e., length of 12A=length of 13A, length of 12B=length of 13B, etc.), a parallelogram is then created upon expansion of the implant, which insure parallelism between segments AD and BC (FIG. 2C). By modifying the lengths of L1 and L2, the four bar linkage is no longer a parallelogram, but rather an angle between plate 6 and 7 occurs. The angle formed may also be dependent on how close ends 20 and 21 are drawn near to each other. As the implant is opened-out, the angle slowly increases.

FIGS. 8-16 relate to a second embodiment of an expansible implant 101, the elements of which are functionally similar to the corresponding elements of the implant embodiment illustrated in FIGS. 1-7. Moreover, the corresponding features in FIGS. 8-16 relating to the embodiment illustrated in FIGS. 1-7 include the same reference numerals, respectively, with the addition of the number 100 and therefore will not be described further.

Figure 9:
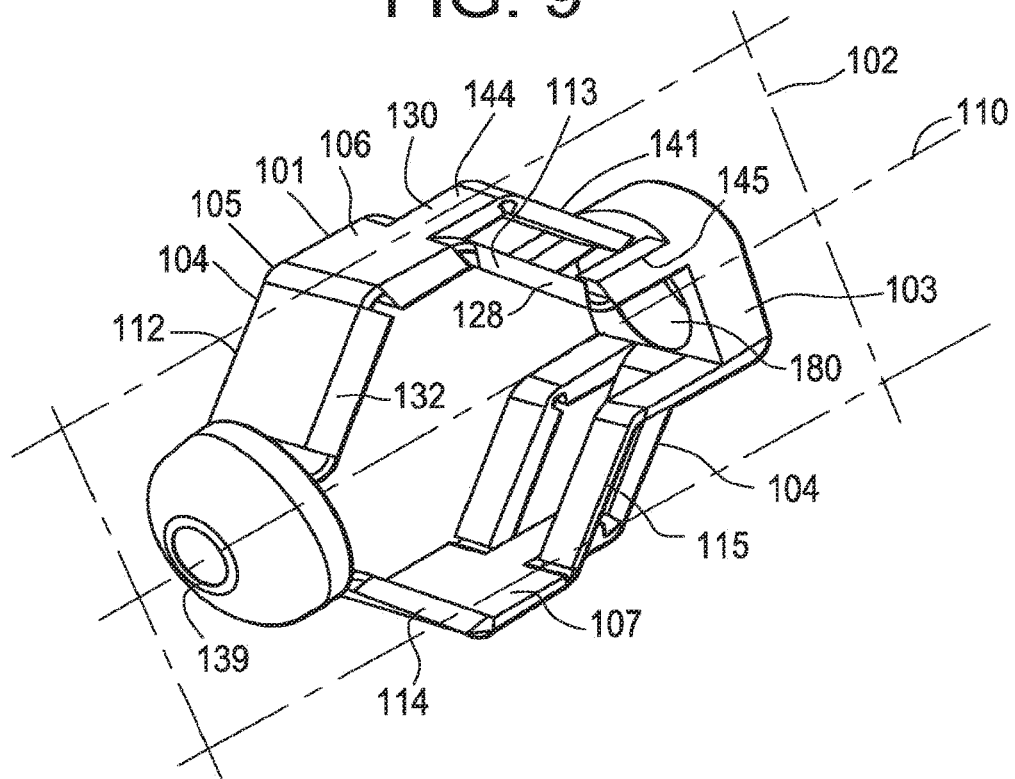
FIG. 9 illustrates the example of FIG. 8, in opened-out position.

The represented implant 101 differs from the implant 1 by the absence of the wing portion on the plates 106 and 107, as represented more particularly in FIG. 9. Implant 101 includes a deformable parallelogram system 141 on one of rigid parts 128 or 132 of each of the arms 122 (upper) and 123 (lower). In the illustrated example, the parallelogram system is represented on rigid part 128 of upper arm 122, connected to the end 120 and the corresponding system on lower arm 123. The parallelogram systems may be used to ensure displacement of the plates of each of the arms 122 and 123, parallel to longitudinal axis 110 of the implant. As represented in the figures, the rigid part 128 of the arm 122 (similarly on corresponding arm 123) is split, as are articulations 131 and 129 (respectively) over the central part 130 and over the end 120 of the implant in order to form a parallelogram which is deformable during displacement of the corresponding plate.

The articulations of the deformable parallelogram 141 may be produced in the same manner as the other articulations 131, 133, 134 of the arm 122, as represented in FIGS. 8-16. The disclosed geometry as explained above and represented in FIGS. 11-14, establishes force couples on the various parts 129, 130, 132 of the arm. This allows for the desired displacements when bringing together ends 120 and 121 of the implant 101.

In order to obtain a deformable parallelogram 141, the rigid part 128 of the arm is preferably divided into three longitudinal levers: two lateral levers 142 and a central lever 143, which form two sides of the deformable parallelogram 141. The two remaining sides of the parallelogram may be formed by an extension 144 of the central part of the arm 122, placed in an axis of extension of the central lever 143, and by a double extension 145 of the end 120, extending parallel to the longitudinal axis 110 of the implant and placed in the axis of extension of the two lateral levers 142 (see FIG. 8).

It is worth noting that arms 122 and 123 may be symmetrical with respect to a plane which is substantially perpendicular to the plane of expansion 102 passing through the longitudinal axis 110 of the implant 101 in order to obtain, during the expansion of the implant, the displacement of the two plates 106 and 107 in a manner parallel to the longitudinal axis 110.

Bone Restoration Examples

A first example of a method for human bone restoration according to one embodiment of the present invention using an expansible implant will now be described with reference to FIGS. 17-29. It concerns, more particularly, a method for bone restoration of a vertebra via a posterolateral route, with fracture reduction. Accordingly, the method may include one or more (and preferably all) of the following steps. One of skill in the art will appreciate that the implant according to so embodiments of the present invention pushes though/divides tissues in the interior of the bone so that the bearing surfaces of the implant preferably come into contact with the bone tissue for restoration.

Figure 17:
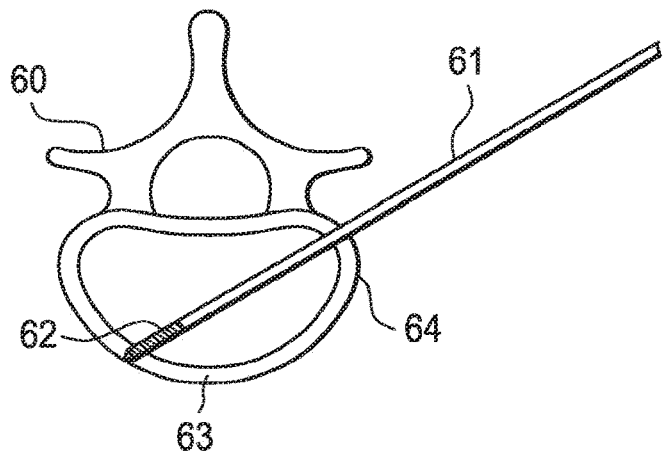
FIGS. 17-29 illustrate schematically, steps for a method for one embodiment for bone restoration according to the invention.
Figure 18:
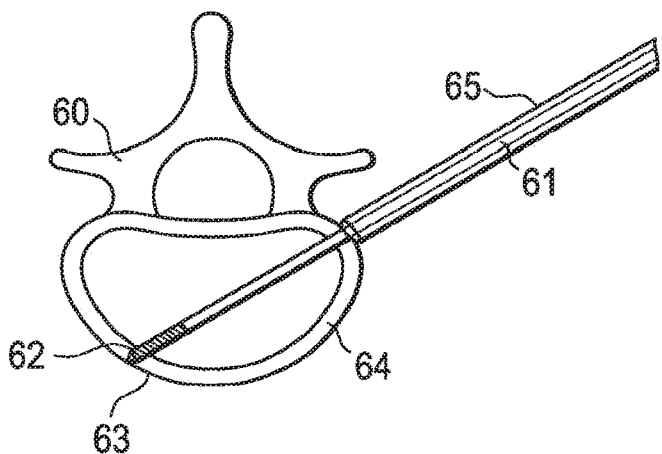

An expansible implant, expansible (preferably) in a single, determined, expansion plane 2 (intrinsic to the implant) is introduced into a vertebra 60, the shape of which is to be restored. To effect this operation, a rod/pin 61 (e.g., Kirschner pin type) is placed percutaneously via the posterolateral route so that the threaded end 62 can be affixed (e.g., screwed) into the cortical bone 63 opposite the cortical bone 64 which is traversed by the pin (FIG. 17). The pin 61 is received in a first dilation tube 65 until an end of the first tube 65 contacts (e.g., may be supported) the exterior surface of the cortical bone 64 (FIG. 18).

Figure 19:
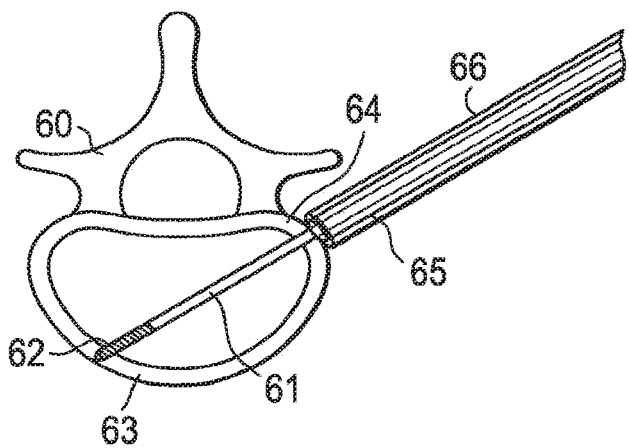
Figure 20:
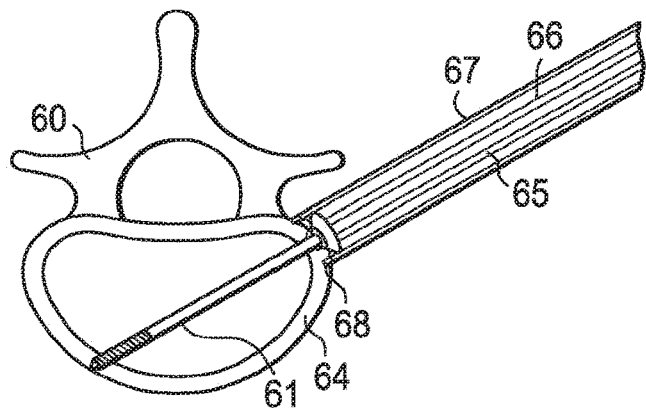

The first dilation tube 65 is received by a second dilation tube 66, until the end of the second tube 66 comes into contact (e.g., supported by) the exterior surface of the cortical bone 64 (FIG. 19). The second dilation tube is further received by a third dilation tube 67, which comes into contact (e.g. is supported) on the exterior surface of the cortical bone 64 (FIG. 20). Teeth on the end of the third dilation tube 67 anchor the tube in the cortical bone 64.

Figure 21:
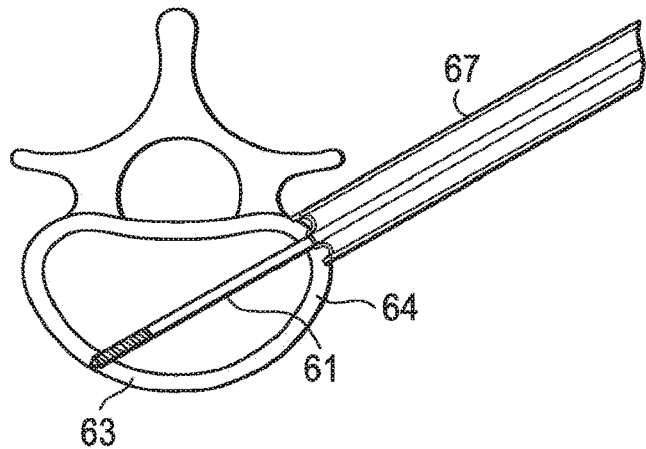
Figure 22:
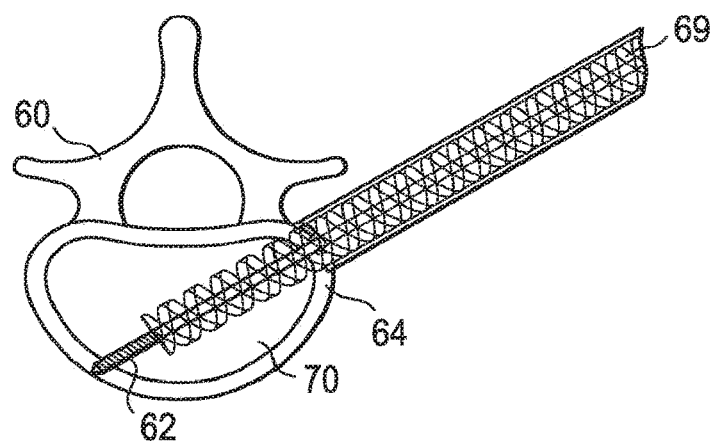

The first 65 and second 66 dilation tubes, as shown in FIG. 21, are then removed, leaving only the pin 61 surrounded by tube 67, which are separated from one another by tubular spacer 68. The proximal cortical bone 64 and cancellous bone 70 is then pierced by means of a drill 69 (for example) guided by the pin 61, as represented in FIG. 22. In one embodiment, the cancellous bone is pierced as far as the distal third (approximately), then the drill 69 may be withdrawn (the pin 61 may be withdrawn as well).

Figure 23:
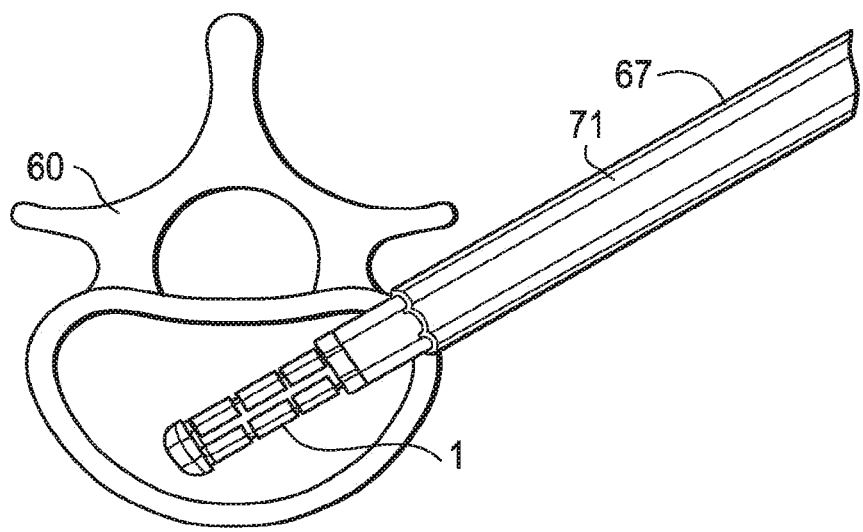

A proximal end of the implant 1 is removably attached to a distal end of a hollow core (preferably) implant carrier 71 which is then introduced into the core of tube 67, as represented in FIG. 23. The implant may be removably affixed to the implant carrier via threaded engagement (for example). Within the core of the implant carrier 71, a rod 72 (see also FIG. 33, reference numeral 3316) having a distal end which includes an engagement means to engage the distal end of the implant (and which may also include an expanded proximal end, larger than a diameter of the rod) may be inserted. Similar to the affixation of the implant to the implant carrier, the engagement means of the rod to the implant may be via threaded engagement.

Figure 33:
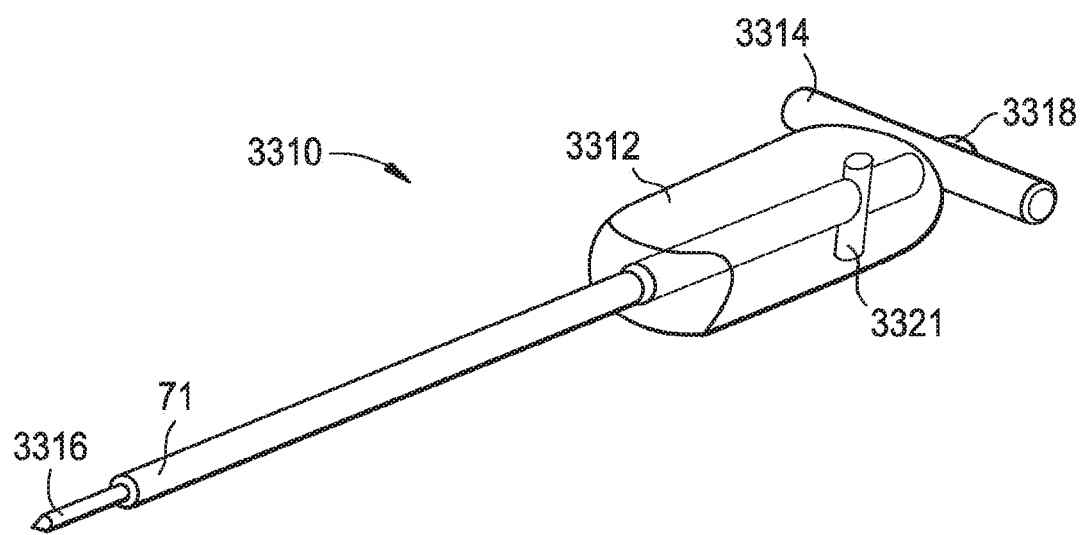
FIG. 33 illustrates a perspective, functional view of an implant carrier device for inserting an implant into the bone of a patient according to one embodiment of the present invention.
Figure 37:
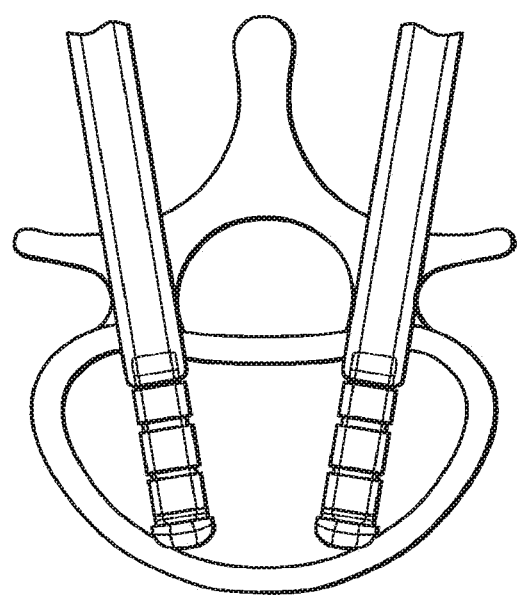
FIG. 37 illustrates the use of a pair of implants according to an embodiment of the present invention.

The implant carrier 71, as shown in FIG. 33, includes a handling means 3310 for controlled movement of the rod relative to the implant carrier (for example). The handing means may comprise a gripping block 3312, having a central bore through which the implant carrier 71 is positioned and is held in place at least rotationally, but preferably rotationally and linearly. In that regard, a proximal end of the gripping member and the proximal end of the implant carrier are preferably flush. A handle 3314, according to one embodiment of the invention, may be attached to the proximal end of either or both of the gripping member and the implant carrier, but is preferably free to rotate relative thereto in either or both of the clockwise and counterclockwise directions. In still another embodiment of the invention, the handle may not be attached to either or both of the gripping block and implant carrier. The handle may include a center opening which preferably includes internal screw threads of a predetermined thread pitch.

The rod 3316, which is received within the implant carrier, preferably includes external threads corresponding in thread pitch to that of handle 3314. A locking device slides relative to the gripping block and may include a pin 3321 which frictionally interferes with the rod 3316, to lock the rod in place (i.e., no rotational movement).

The threads of the rod are preferably provided at least along a majority of the length rod. According to one embodiment of the invention, the rod, implant carrier, gripping block and handle may be pre-assembled. One would insert the threaded distal end of the rod into an opening in the center of the proximal end of the implant, where it then may be received in the correspondingly threaded portion in the center of the distal end of the implant. The distal end (i.e., the location of the implant) of the assembly of the implant with the implant carrier/handling means may then be inserted into dilation tube 67.

Figure 34:
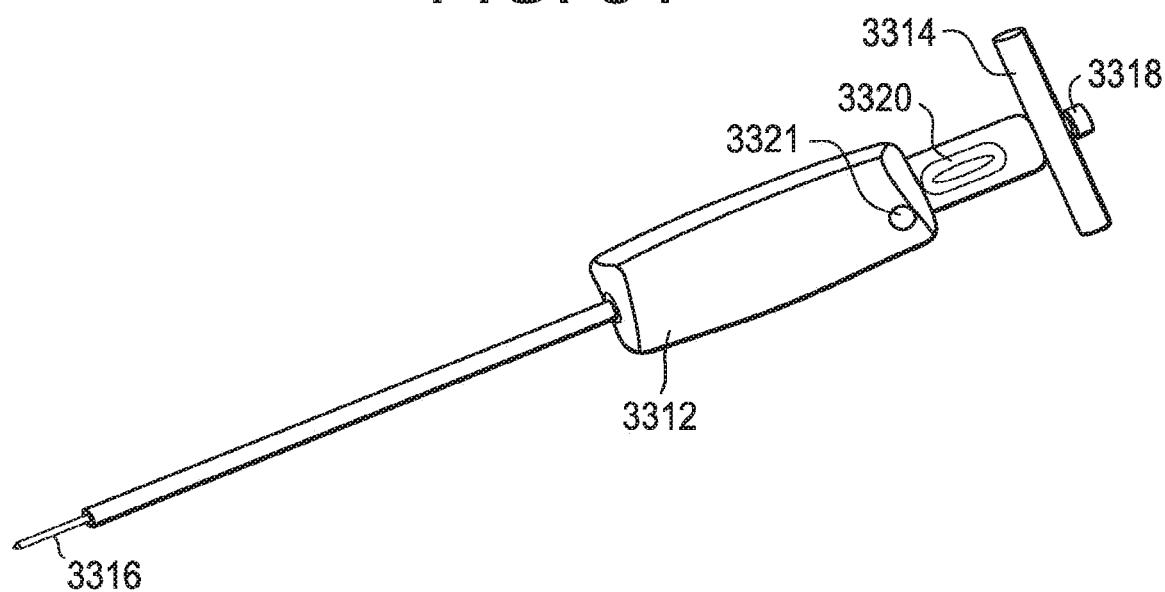
FIG. 34 illustrates a top view of the implant carrier device of FIG. 33.
Figure 35:
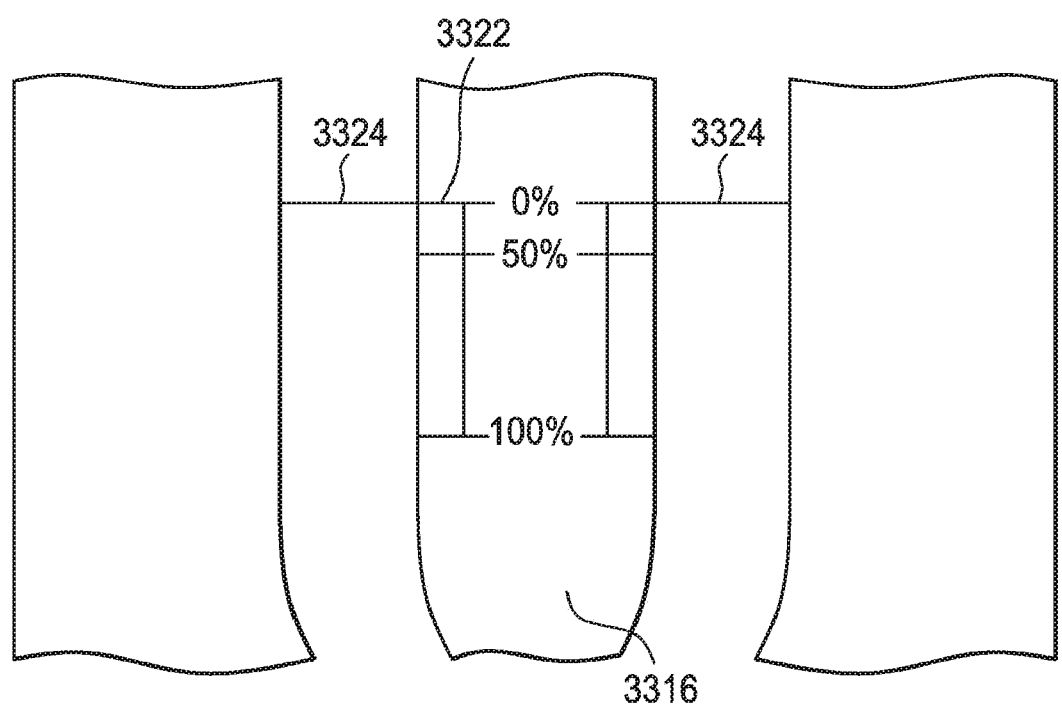
FIG. 35 illustrates an expansion gauge for the implant carrier shown in FIGS. 33 and 34.

FIG. 34 illustrates another view of the implant carrier, and includes a gauge 3320 which may be used to indicate the amount of expansion of the implant (e.g., a determination on the rotation amount of the rod 3316). The gauge may comprise a window to the rod 3316. As show in FIG. 35, according to one embodiment of the invention, the portion of the rod that is visible may not include threads. Rather, this section of the rod may include markings 3322 which indicate a percentage of expansion. Additional markings 3324 provided adjacent the window allow a user to gauge the percentage of expansion from the relative movement between the two markings.

Figure 36:
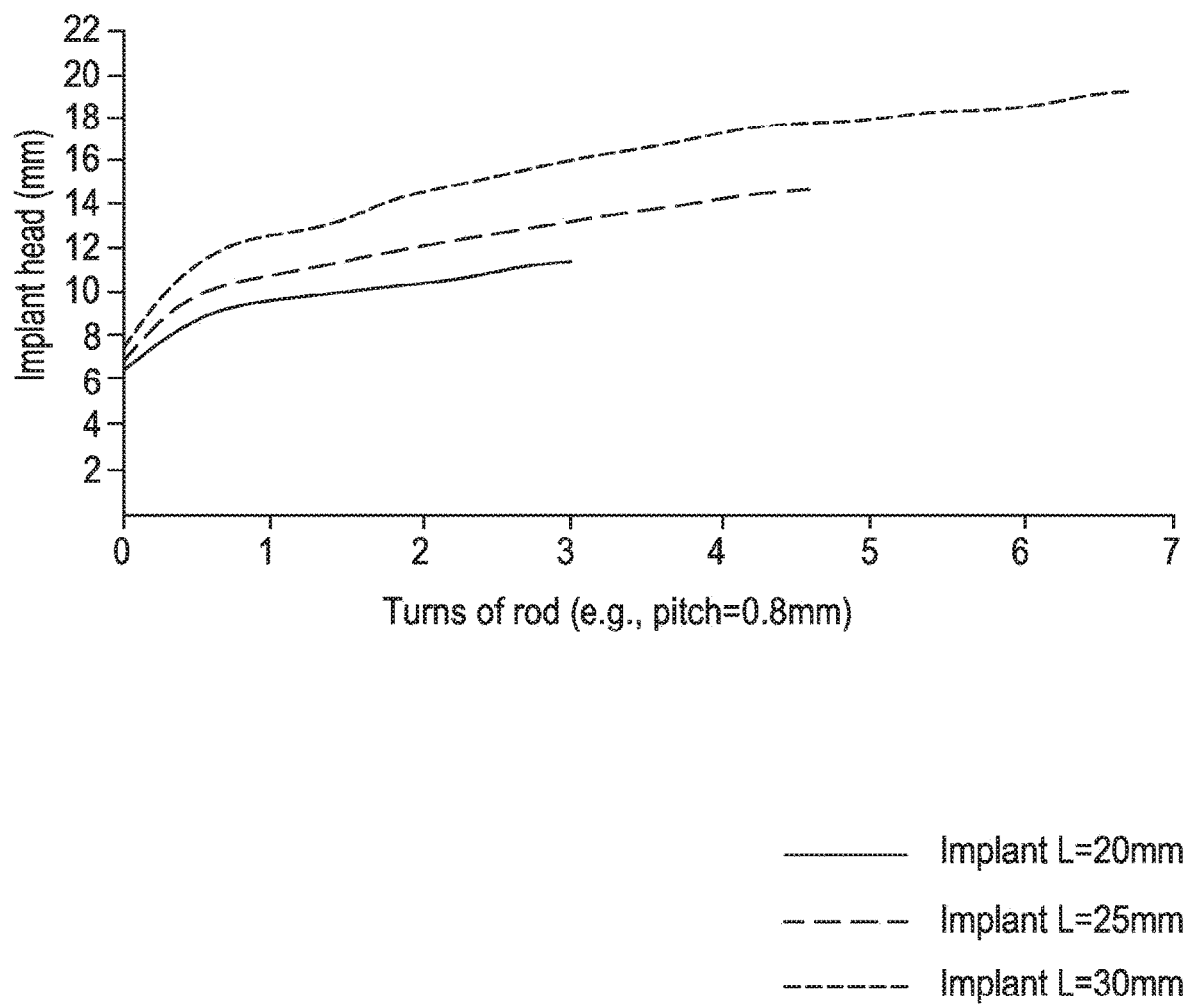
FIG. 36 is a graph illustrating expansion of implants according to some of the disclosed embodiments using the implant carrier shown in FIGS. 33 and 34.

Depending upon the predetermined thread pitch and direction of the thread of the rod 3316, rotation of the handle moves the rod 3316 relative to the implant carrier linearly in a direction. Preferably, the threads are provided on the rod such that clockwise rotation of the handle moves the rod outward away from an area in which the implant is to expand (the implantation area). For example, for an M5 thread, a pitch of 0.8 mm may be used. However, one of skill in the art will appreciate that a thread pitch of between about 0.5 mm and about 1.0 mm (for example) may be used. FIG. 36 is a chart illustrating a no-load expansion of an implant according to one of the embodiments of the invention by the number of turns of the rod for three particular sizes of implants.

Figure 24:
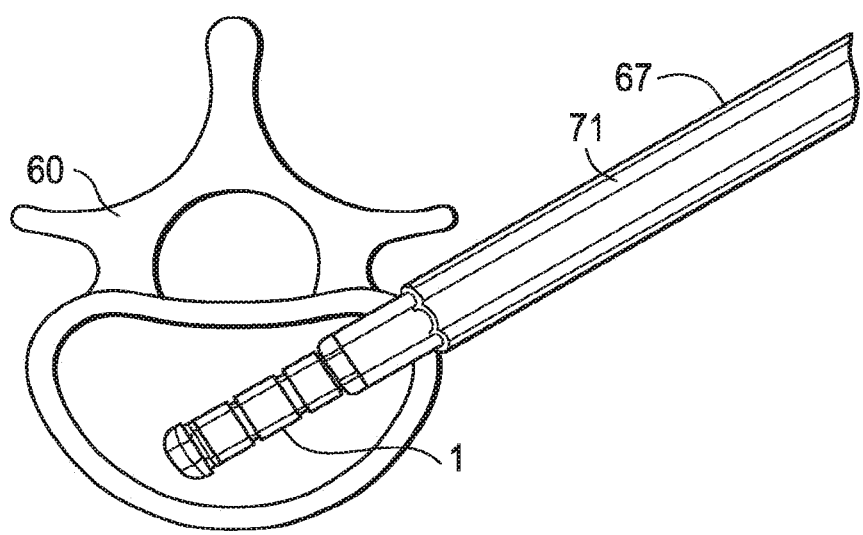

Accordingly, in view of the above embodiment, once the implant is positioned within the dilation tube and slid down therein, so that it is placed into the interior of the vertebra 60. The implant is preferably positioned such that the single expansion plane 2 corresponds to the desired bone restoration plane (FIG. 24). The position of the implant may be verified using any known imaging techniques, including, for example, X-ray and ultrasound.

Figure 25:
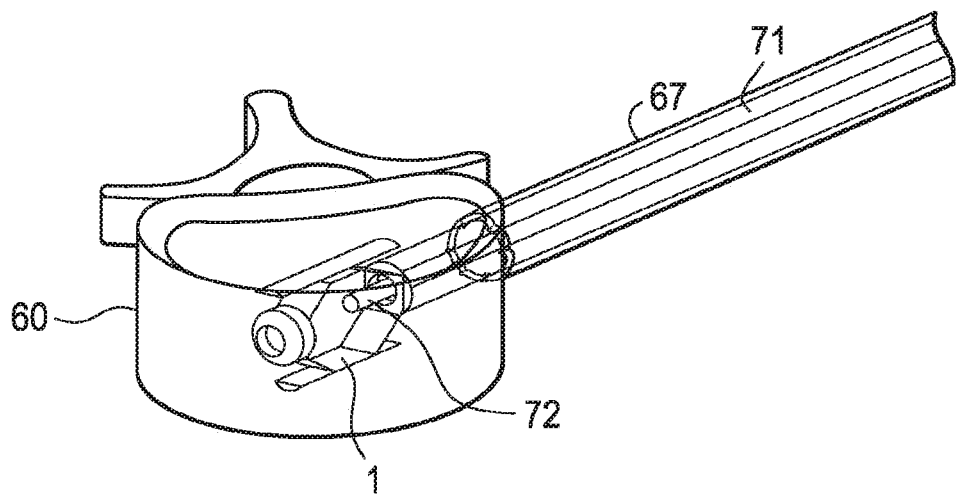
Figure 26:
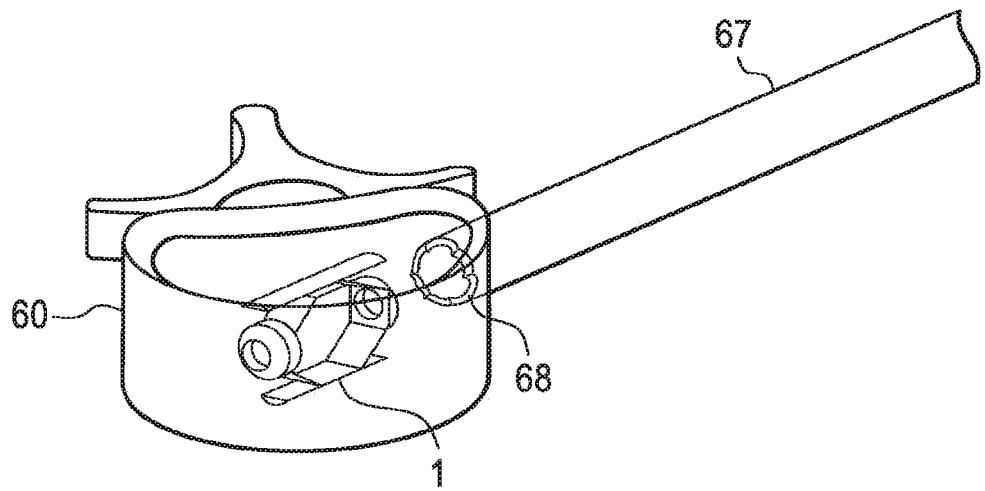

The handle 3314 is then rotated to "pull" the rod away from the implantation area. Since the proximal end of the implant is butted up against the implant carrier, and pulling on the rod causes the distal end of the implant to move toward the proximal end (or visa-versa). This results in the ends of the implant drawing towards each other which opens out the implant. More specifically, opposite plates 6 and 7 are opened out, advantageously forming, respectively, a first 8 and a second 9 support surface in the vertebra 60, which surfaces may be continuous over their length which may be substantially equal to the length of the implant 1 (FIG. 25). In the course of the expansion, control of the reduction of the fracture thanks to the millimetric control means, and after having obtained the desired expansion, for example of a determined value between a minimum thickness of the implant before any expansion of the latter and a maximum thickness of the implant after its maximum expansion, then freeing of the implant carrier 71 by unscrewing it from the implant 1, then extraction of the tube 67, as represented in FIG. 26, with the implant in opened-out position remaining in place in the vertebra 60.

Accordingly, the expansion of the implant in the vertebra is achieved by support under the plates allowing the thrust force to be distributed over the length of the plates under the latter. Thus a sufficient length of the plates may be provided while limiting an excessive dimensioning of the thickness of the latter in order to resist flexion. It will be appreciated by those of ordinary skill in the art that the implant according to some embodiments of the invention adopts a ratio of a spatial requirement in length (un-expanded) to length of elevated plate which is extremely optimized, allowing a preferable use of the limited intra-osseous spaces with a view to fracture reduction, for example.

The rod 3316 may also include, according to one of the embodiments of the invention, a disengagement means, which may comprise an internal hex on the proximal end 3318 of the rod. This may allow one to disengage the rod from the implant once the implant has been opened out. Alternatively, where the handle is not attached to the gripping block and/or implant carrier, the handle could be counter-rotated (i.e., rotated such that the rod does not move in a direction away from the implant) such that it travels away from the flush portion of the gripping block and implant carrier, such that it engages the proximal end of the rod. Further counter-rotation of the handle (after opening out of the implant) causes the rod to rotate in the same counter-rotation as the handle, thereby causing the rod to disengage from the implant. Depending upon the determined thread pitch, such disengagement can occur in any number of rotations (e.g., less or more than one rotation). See also FIG. 26.

Figure 27:
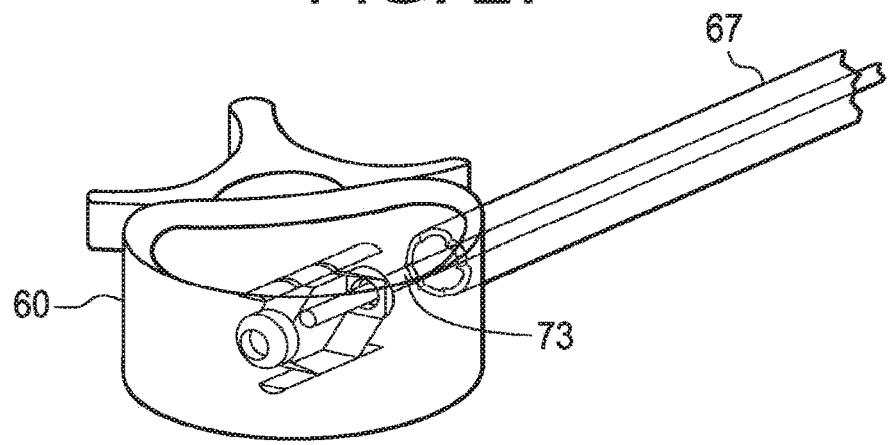
Figure 28:
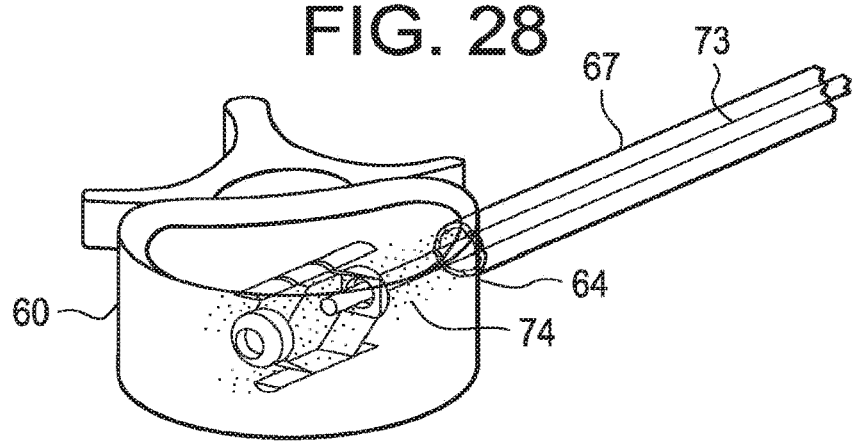
Figure 29:
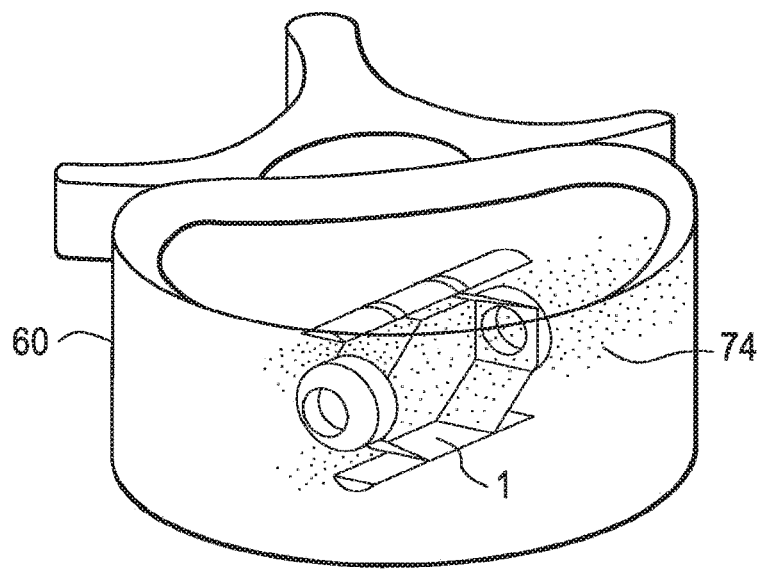

Preferably, after the rod has been removed, a filling material 74 is injected around the implant. The filling material may comprise, for example, an ionic cement, in particular, a phosphocalcic cement, an acrylic cement or a compound of the latter, with a view to filling in and around the implant. To accomplish this, a needle of the injector 73 is slid down tube 67 until the end of the needle reaches the distal orifice 39 of the implant 1 (FIG. 27). The filling material is then injected via the needle. Continued injection in a retrograde manner may be done up to a proximal orifice in cortical bone 64 of the vertebra 60 (FIG. 28). The needle of the injector may then be withdraw from tube 67 (FIG. 29).

Figure 30:
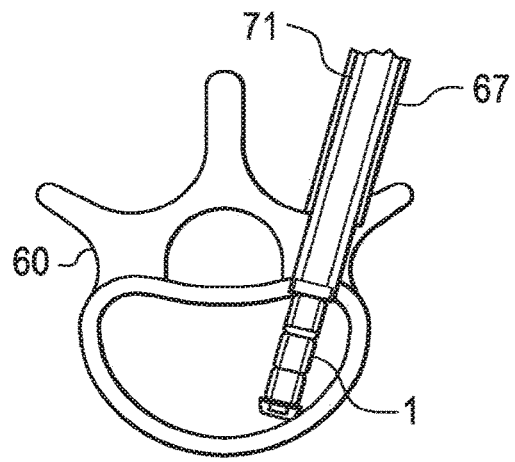
FIGS. 30-32 illustrate schematically, steps for another method for bone restoration according to the invention.
Figure 31:
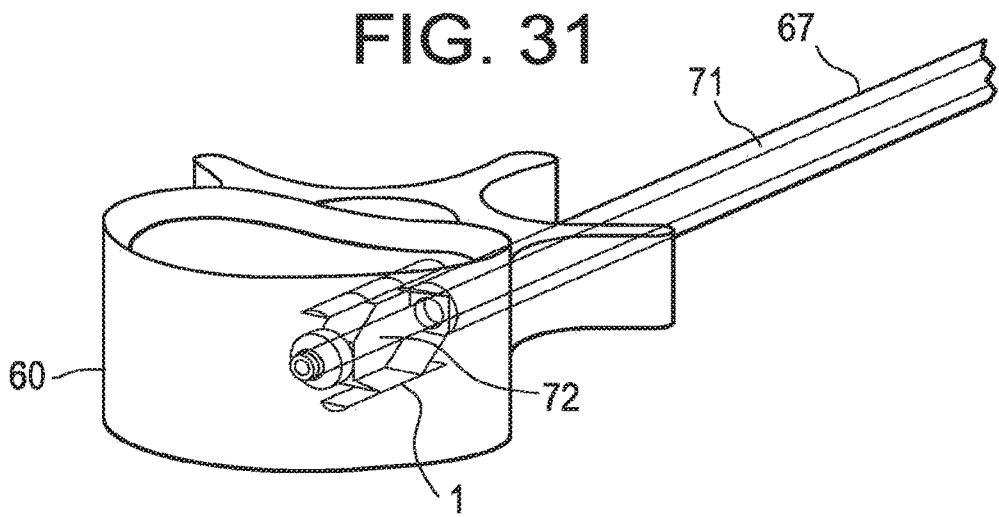
Figure 32:
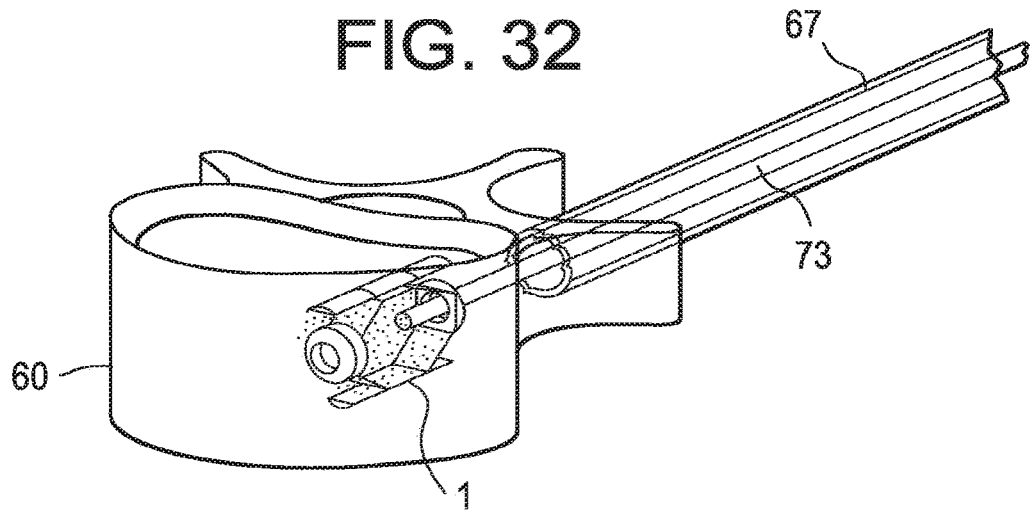

A second example of a method according to an embodiment of the invention for restoration of human bone anatomy, will now be described with references to FIGS. 30-32. This example generally concerns a method for bone restoration of a vertebra by a transpedicular route, with fracture reduction.

The second example is similar to the first and differs from the latter by the penetration route of the implant into the vertebra 60, which is now accomplished in a transpedicular manner (FIG. 30) instead of the posterolateral route used in the first method. As a result, only some steps of the second method have been represented in FIGS. 30-32 in order to show the different route used for the introduction of the implant 1 into the vertebra. For FIGS. 30 to 32, elements identical to those of the first method example have the same numerical references, and those figures correspond respectively to the steps of FIGS. 24, 25 and 28 of the first method example. Concerning the step represented in FIG. 32, the latter differs slightly from FIG. 28 by the position of the needle of the injector 73, closer to the distal end of the implant in FIG. 32.

It will thus be seen that the invention attains the objects made apparent from the preceding description. Since certain changes may be made without departing from the scope of the present invention, it is intended that all matter contained in the above description or shown in the accompanying drawings be interpreted as illustrative and not in a literal sense (and thus, not limiting). Practitioners of the art will realize that the method, device and system configurations depicted and described herein are examples of multiple possible system configurations that fall within the scope of the current invention.

What is claimed is:

1. A system for restoring a vertebral body, said system comprising:
    an introducer tube;
    an implant comprising:
        an end element defining an opening;
        plates each defining a bearing surface configured to be moved away from one another to expand said implant within the vertebral body; and
        supports each coupled to one of said plates, wherein said supports comprise a reduced thickness portion defining a material web configured to plastically deform during expansion of said implant;
    an implant carrier with which said end element of said implant is removably coupled during insertion of said implant through said introducer tube and into the vertebral body; and
    a rod configured to be directed through said implant carrier, wherein said rod is configured to be translated relative to said implant carrier to cause expansion of said implant,
    wherein said plates are configured to be moved away from one another to a non-parallel state in which said plates angle away from one another.

2. The system of claim 1, wherein said non-parallel state is further defined by ends of said plates opposite said end element being spaced farther apart than opposing ends of said plates nearer said end element.

3. The system of claim 1, wherein said rod is further configured to be directed through said opening of said end element.

4. The system of claim 1, further comprising a drill configured to be directed through said introducer tube and operated to establish an enlarged opening within the vertebral body for insertion of said implant.

5. The system of claim 1, further comprising a handle with which said rod is threadably coupled, and wherein said implant carrier comprises a gripping block configured to translate said rod relative to said implant carrier without rotation of said rod relative to said gripping block.

6. The system of claim 1, further comprising a filling cement configured to be injected within a void defined by said implant, and around said implant.

7. The system of claim 6, wherein filling cement is further configured to be directed through said opening of said end element.

8. The system of claim 1, wherein said supports are first supports, said implant further comprising a second supports each coupled to said end element and one of said plates, wherein said second supports comprise a material web configured to plastically deform during expansion of said implant.

9. A system for restoring a vertebral body, said system comprising:
an introducer tube;
an implant comprising:
an end element defining a first opening;
plates each defining a bearing surface configured to be moved away from one another to expand said implant within the vertebral body; and
supports each coupled to one of said plates and configured to plastically deform during expansion of said implant;
an opposed portion coupled to said supports and defining a second opening coaxially aligned with said first opening, wherein said opposed portion is configured to receive a longitudinal force to be moved relative to said end element for expanding said implant;
an implant carrier with which said end element of said implant is removably coupled during insertion of said implant through said introducer tube and into the vertebral body;
a handle; and
a rod threadably coupled to said handle and configured to be directed through said implant carrier and said first opening of said end element, wherein said rod is configured to be provide said longitudinal force to said opposed portion,
wherein said implant carrier comprises a gripping block configured to translate said rod relative to said implant carrier without rotation of said rod relative to said gripping block.

10. The system of claim 9, wherein said plates are configured to be moved away from one another to a non-parallel state in which said plates angle away from one another.

11. The system of claim 10, wherein said non-parallel state is further defined by ends of said plates opposite said end element being spaced farther apart than opposing ends of said plates nearer said end element.

12. The system of claim 9, further comprising a drill configured to be directed through said introducer tube and operated to establish an enlarged opening within the vertebral body for insertion of said implant.

13. The system of claim 9, further comprising a filling cement configured to be injected within a void defined by said implant, and around said implant.

14. The system of claim 13, wherein filling cement is further configured to be directed through said first opening of said end element.

15. The system of claim 9, wherein said supports are parallel to said plates prior to expansion of said implant.

16. A system for restoring a vertebral body, said system comprising:
an introducer tube;
an implant comprising:
an end element defining an opening;
plates each defining a bearing surface and configured to be moved away from one another to a non-parallel state in which said plates angle away from one another and in which ends of said plates opposite said end element are spaced farther apart than opposing ends of said plates nearer said end element, wherein said implant is configured to be expanded within the vertebral body in said non-parallel state;
a support coupled to each of said plates and configured to plastically deform during expansion of said implant;
an implant carrier with which said end element of said implant is removably coupled during insertion of said implant through said introducer tube and into the vertebral body; and
a rod configured to be directed through said implant carrier, wherein said rod is configured to be translated relative to said implant carrier to cause expansion of said implant.

17. The system of claim 16, wherein said support comprises a reduced thickness portion defining a material web configured to plastically deform.

18. The system of claim 16, wherein said opening is a first opening, said implant further comprising an opposed portion coupled to said supports and defining a second opening coaxially aligned with said first opening, wherein said opposed portion is configured to receive a longitudinal force to be moved relative to said end element for expanding said implant.

19. The system of claim 16, wherein said supports are parallel to said plates prior to expansion of said implant.

20. An implant for restoring a vertebral body, said implant comprising:
an end element defining an opening;
plates each defining a bearing surface configured to be moved away from one another to a non-parallel state in which said plates angle away from one another and in which ends of said plates opposite said end element are spaced farther apart than opposing ends of said plates nearer said end element, wherein said implant is configured to be expanded said implant within the vertebral body in said non-parallel state; and
a support coupled to each of said plates, wherein said support comprises a reduced thickness portion defining a material web configured to plastically deform during expansion of said implant.

21. The implant of claim 20, further comprising an opposed portion coupled to said supports and configured to receive a longitudinal force to be moved relative to said end element for expanding said implant.

22. The implant of claim 21, wherein said opening is a first opening, wherein said opposed portion defines a second opening coaxially aligned with said first opening.

23. The implant of claim 20, wherein said supports are first supports, said implant further comprising second supports each coupled to said end element and one of said plates, wherein said second supports comprise a material web configured to plastically deform during expansion of said implant.

* * * * *